United States Patent [19]
Collett et al.

[11] Patent Number: 4,735,800
[45] Date of Patent: Apr. 5, 1988

[54] VACCINES AGAINST RIFT VALLEY FEVER VIRUS

[75] Inventors: Marc S. Collett, Minnetonka, Minn.; Anthony F. Purchio, Seattle, Wash.

[73] Assignee: Molecular Genetics, Inc., Minnetonka, Minn.

[21] Appl. No.: 642,781

[22] Filed: Aug. 23, 1984

Related U.S. Application Data

[63] Continuation-in-part of Ser. No. 530,887, Sep. 9, 1983, abandoned.

[51] Int. Cl.$^4$ .................. A61K 39/12; C12P 21/00; C12N 15/00; C12N 1/20; C12N 1/00; C07H 15/12

[52] U.S. Cl. .................... 424/89; 435/68; 435/172.3; 435/253; 435/317; 435/849; 536/27; 935/22; 935/65; 530/806

[58] Field of Search .............. 435/68, 172.3, 253, 435/317; 536/27; 424/89; 935/22, 65; 530/350, 403, 806

[56] References Cited

U.S. PATENT DOCUMENTS

| | | | |
|---|---|---|---|
| 4,237,224 | 12/1980 | Cohen et al. | 435/68 |
| 4,304,863 | 12/1981 | Collins et al. | 435/172.3 |
| 4,399,216 | 8/1983 | Axel et al. | 435/68 |

OTHER PUBLICATIONS

Kornberg, *DNA Replication*, Freeman & Co., San Francisco, 1980, pp. 637–639.
Purchio et al., 1984, Production of a Subunit Vaccine for Rift Valley Fever Virus, IN: Molecular Biology of Negative Strand Viruses (eds. P. L. Bishop and R. W. Compans) Academic Press, pp. 159–166.
Collett et al., 1985, Molecular Characterization of the M RNA Segment of the Rift Valley Fever Virus, IN: Veterinary Viral Diseases. Their Significance in South-East Asia and the Western Pacific (eds. A. D. Della Parta) Academic Press, pp. 415–418.
Collett et al., 1985, Virol. 144:228–245.
Cash et al., 1981, Biochemical Characterization of Rift Valley Fever Virus and Other Phlebotomus Fever Group Virus, IN Contrl. to Epid. Biostatist. (ed. Klinberg, Karager, Basel) vol. 3, pp. 1–20.
Rice et al., 1980, Virology, 105: 256–260, Biochemical Characterization of Rift Valley Fever Virus.
Struthers and Swanepoel, 1982, J. Gen. Virol. 60: 381–384, Identification of a Major Non-Structural Protein in the Nuclei of Rift Valley Fever-Infected Cells.
Bachrach, 1982, JAVMA, 181: 992–999, Recombinant DNA Technology for the Preparation of Subunit Vaccines.
Niklasson, 1982, Scand. J. Infect. Dis., 14: 105–109, Rift Valley Fever Virus Vaccine Trial Study of Side Effects in Humans.
Kark et al., 1982, Amer. J. Epidem., 116: 808–820, A Rift Valley Fever Virus Trial.

*Primary Examiner*—Esther M. Kepplinger
*Assistant Examiner*—Shawn P. Foley
*Attorney, Agent, or Firm*—Pennie & Edmonds

[57] ABSTRACT

Methods and compositions are provided for the cloning and expression of Rift Valley Fever Virus genes in single cell host organisms. Also described are methods for culturing these novel single-cell organisms to produce Rift Valley Fever Virus gene gene products which may be formulated for use as products which may be formulated for use as immunogens in vaccines to protect against Rift Valley Fever Virus infections.

88 Claims, 11 Drawing Sheets

FIG. 2a

```
                                                    AC ACA AAG ACG GTG CAT TAA        20
                                                       Thr Lys Thr Val His ***

ATG TAT GTT TTA TTA ACA ATT CTA ATC TCG GTT CTG GTG TGT GAA GCG GTT ATT AGA GTG   80
  1 Met Tyr Val Leu Leu Thr Ile Leu Ile Ser Val Leu Val Cys Glu Ala Val Ile Arg Val

TCT CTA AGC TCC ACA AGA GAA GAG ACC TGC TTT GGT GAC TCC ACT AAC CCA GAG ATG ATT  140
 21 Ser Leu Ser Ser Thr Arg Glu Glu Thr Cys Phe Gly Asp Ser Thr Asn Pro Glu Met Ile

GAA GGA GCT TGG GAT TCA CTC AGA GAG GAG GAG ATG CCG GAG GAG CTC TCC TGT TCT ATA  200
 41 Glu Gly Ala Trp Asp Ser Leu Arg Glu Glu Glu Met Pro Glu Glu Leu Ser Cys Ser Ile

TCA GGC ATA AGA GAG GTT AAG ACC TCA AGC CAG GAG TTA TAC AGG GCA TTA AAA GCC ATC  260
 61 Ser Gly Ile Arg Glu Val Lys Thr Ser Ser Gln Glu Leu Tyr Arg Ala Leu Lys Ala Ile
                                                              BamHI
    ATT GCT GCT GAT GGC TTG AAC AAC ATC ACC TGC CAT GGT AAG GAT CCT GAG GAC AAG ATT  320
 81 Ile Ala Ala Asp Gly Leu Asn Asn Ile Thr Cys His Gly Lys Asp Pro Glu Asp Lys Ile

TCC CTC ATA AAG GGT CCT CCT CAC AAA AAG CGG GTG GGG ATA GTT CGG TGT GAG AGA CGA  380
101 Ser Leu Ile Lys Gly Pro Pro His Lys Lys Arg Val Gly Ile Val Arg Cys Glu Arg Arg

AGA GAT GCT AAG CAA ATA GGG AGA GAA ACC ATG GCA GGG ATT GCA ATG ACA GTC CTT CCA  440
121 Arg Asp Ala Lys Gln Ile Gly Arg Glu Thr Met Ala Gly Ile Ala Met Thr Val Leu Pro
                                                            G2
    GCC TTA GCA GTT TTT GCT TTG GCA CCT GTT GTT TTT GCT GAA GAC CCC CAT CTC AGA AAC  500
141 Ala Leu Ala Val Phe Ala Leu Ala Pro Val Val Phe Ala Glu Asp Pro His Leu Arg Asn

AGA CCA GGG AAG GGG CAC AAC TAC ATT GAC GGG ATG ACT CAG GAG GAT GCC ACA TGC AAA  560
161 Arg Pro Gly Lys Gly His Asn Tyr Ile Asp Gly Met Thr Gln Glu Asp Ala Thr Cys Lys

CCT GTG ACA TAT GCT GGG GCA TGT AGC AGT TTT GAT GTC TTG CTT GAA AAG GGA AAA TTT  620
181 Pro Val Thr Tyr Ala Gly Ala Cys Ser Ser Phe Asp Val Leu Leu Glu Lys Gly Lys Phe

CCC CTT TTC CAG TCG TAT GCT CAT CAT AGA ACT CTA CTA GAG GCA GTT CAC GAC ACC ATC  680
201 Pro Leu Phe Gln Ser Tyr Ala His His Arg Thr Leu Leu Glu Ala Val His Asp Thr Ile

ATT GCA AAG GCT GAT CCA CCT AGC TGT GAC CTT CAG AGT GCT CAT GGG AAC CCC TGC ATG  740
221 Ile Ala Lys Ala Asp Pro Pro Ser Cys Asp Leu Gln Ser Ala His Gly Asn Pro Cys Met

AAA GAG AAA CTC GTG ATG AAG ACA CAC TGT CCA AAT GAC TAC CAG TCA GCT CAT TAC CTC  800
241 Lys Glu Lys Leu Val Met Lys Thr His Cys Pro Asn Asp Tyr Gln Ser Ala His Tyr Leu

AAC AAT GAC GGG AAA ATG GCT TCA GTC AAG TGC CCT CCT AAG TAT GGG CTC ACT GAG GAC  860
261 Asn Asn Asp Gly Lys Met Ala Ser Val Lys Cys Pro Pro Lys Tyr Gly Leu Thr Glu Asp

TGC AAC TTT TGT AGG CAG ATG ACA GGT GCT AGC CTG AAG AAG GGG TCT TAT CCT CTC CAA  920
281 Cys Asn Phe Cys Arg Gln Met Thr Gly Ala Ser Leu Lys Lys Gly Ser Tyr Pro Leu Gln

GAC TTG TTT TGT CAG TCA AGT GAG GAT GAT GGA TCA AAA TTA AAA ACA AAA ATG AAA GGG  980
301 Asp Leu Phe Cys Gln Ser Ser Glu Asp Asp Gly Ser Lys Leu Lys Thr Lys Met Lys Gly

GTC TGC GAA GTG GGG GTT CAA GCA CAC AAA AAG TGT GAT GGC CAA CTC AGC ACT GCA CAT 1,040
321 Val Cys Glu Val Gly Val Gln Ala His Lys Lys Cys Asp Gly Gln Leu Ser Thr Ala His
                                                                        HindIII
    GAG GTT GTG CCC TTT GCA GTG TTT AAG AAC TCA AAG AAG GTT TAT CTT GAT AAG CTT GAC 1,100
341 Glu Val Val Pro Phe Ala Val Phe Lys Asn Ser Lys Lys Val Tyr Leu Asp Lys Leu Asp CTT AAG ACT GAG GAG AAT CTG CTA CCA GAC TCA TTT GTC TGT TTC GAG CAT AAG GGA CAG 1,160
361 Leu Lys Thr Glu Glu Asn Leu Leu Pro Asp Ser Phe Val Cys Phe Glu His Lys Gly Gln
                                                        SstI       HindIII
    TAC AAA GGA ACA ATG GAC TCT GGT CAG ACT AAG AGG GAG CTC AAA AGC TTT GAT ATC TCT 1,220
381 Tyr Lys Gly Thr Met Asp Ser Gly Gln Thr Lys Arg Glu Leu Lys Ser Phe Asp Ile Ser CAG TGC CCC AAG ATT GGA GGA CAT GGT AGT AAG AAG TGC ACT GGG GAC GCA GCA TTT TGC 1,280
401 Gln Cys Pro Lys Ile Gly Gly His Gly Ser Lys Lys Cys Thr Gly Asp Ala Ala Phe Cys
```

FIG. 2b

```
          TCT GCT TAT GAG TGC ACT GCT CAG TAC GCC AAT GCC TAT TGT TCA CAT GCT AAT GGG TCA   1,340
      421 Ser Ala Tyr Glu Cys Thr Ala Gln Tyr Ala Asn Ala Tyr Cys Ser His Ala Asn Gly Ser

GGG ATT GTG CAG ATA CAA GTA TCA GGG GTC TGG AAG AAG CCT TTA TGT GTA GGG TAT GAG   1,400
      441 Gly Ile Val Gln Ile Gln Val Ser Gly Val Trp Lys Lys Pro Leu Cys Val Gly Tyr Glu

AGA GTG GTT GTG AAG AGA GAA CTC TCT GCC AAG CCC ATC CAG AGA GTT GAG CCT TGC ACA   1,460
      461 Arg Val Val Val Lys Arg Glu Leu Ser Ala Lys Pro Ile Gln Arg Val Glu Pro Cys Thr

ACT TGT ATA ACC AAA TGT GAG CCT CAT GGA TTG GTT GTC CGA TCA ACA GGG TTC AAG ATA   1,520
      481 Thr Cys Ile Thr Lys Cys Glu Pro His Gly Leu Val Val Arg Ser Thr Gly Phe Lys Ile

TCA TCA GCA GTT GCT TGT GCT AGC GGA GTT TGC GTC ACA GGA TCG CAG AGT CCT TCC ACC   1,580
      501 Ser Ser Ala Val Ala Cys Ala Ser Gly Val Cys Val Thr Gly Ser Gln Ser Pro Ser Thr

GAG ATT ACA CTC AAG TAT CCA GGG ATA TCC CAG TCT TCT GGG GGG GAC ATA GGG GTT CAC   1,640
      521 Glu Ile Thr Leu Lys Tyr Pro Gly Ile Ser Gln Ser Ser Gly Gly Asp Ile Gly Val His

ATG GCA CAC GAT GAT CAG TCA GTT AGC TCC AAA ATA GTA GCT CAC TGC CCT CCC CAG GAC   1,700
      541 Met Ala His Asp Asp Gln Ser Val Ser Ser Lys Ile Val Ala His Cys Pro Pro Gln Asp

CCG TGT TTA GTG CAT GGC TGC ATA GTG TGT GCT CAT GGC CTG ATA AAT TAC CAG TGT CAC   1,760
      561 Pro Cys Leu Val His Gly Cys Ile Val Cys Ala His Gly Leu Ile Asn Tyr Gln Cys His

ACT GCT CTC AGT GCC TTT GTT GTT GTG TTT GTA TTC AGT TCT ATT GCA ATA ATT TGT TTA   1,820
      581 Thr Ala Leu Ser Ala Phe Val Val Val Phe Val Phe Ser Ser Ile Ala Ile Ile Cys Leu

GCT GTT CTT TAT AGG GTG CTT AAG TGC CTG AAG ATT GCC CCA AGG AAA GTT CTG AAT CCA   1,880
      601 Ala Val Leu Tyr Arg Val Leu Lys Cys Leu Lys Ile Ala Pro Arg Lys Val Leu Asn Pro

CTA ATG TGG ATC ACA GCC TTC ATC AGA TGG ATA TAT AAG AAG ATG GTT GCC AGA GTG GCA   1,940
      621 Leu Met Trp Ile Thr Ala Phe Ile Arg Trp Ile Tyr Lys Lys Met Val Ala Arg Val Ala

GAC AAC ATT AAT CAA GTG AAC AGG GAA ATA GGA TGG ATG GAA GGA GGT CAG TTG GTT CTA   2,000
      641 Asp Asn Ile Asn Gln Val Asn Arg Glu Ile Gly Trp Met Glu Gly Gly Gln Leu Val Leu

GGG AAC CCT GCC CCT ATT CCT CGT CAT GCC CCA ATC CCA CGT TAT AGC ACA TAC CTG ATG   2,060
      661 Gly Asn Pro Ala Pro Ile Pro Arg His Ala Pro Ile Pro Arg Tyr Ser Thr Tyr Leu Met
                                                            ──▶ G1
          TTA TTA TTG ATT GTC TCA TAT GCA TCA GCA|TGT TCA GAA CTG ATT CAG GCA AGC TCC AGA   2,120
      681 Leu Leu Leu Ile Val Ser Tyr Ala Ser Ala Cys Ser Glu Leu Ile Gln Ala Ser Ser Arg
                                                Hpa I
          ATC ACC ACT TGC TCT ACA GAG GGT GTT AAC ACC AAG TGT AGA CTG TCT GGC ACA GCA TTG   2,180
      701 Ile Thr Thr Cys Ser Thr Glu Gly Val Asn Thr Lys Cys Arg Leu Ser Gly Thr Ala Leu

ATC AGA GCA GGG TCA GTT GGG GCA GAG GCT TGT TTG ATG TTG AAG GGG GTC AAG GAA GAT   2,240
      721 Ile Arg Ala Gly Ser Val Gly Ala Glu Ala Cys Leu Met Leu Lys Gly Val Lys Glu Asp

CAA ACC AAG TTC TTA AAG ATA AAA ACT GTC TCA AGT GAG CTA TCA TGC AGG GAG GGC CAG   2,300
      741 Gln Thr Lys Phe Leu Lys Ile Lys Thr Val Ser Ser Glu Leu Ser Cys Arg Glu Gly Gln

AGT TAT TGG ACT GGG TCC ATT AGC CCT AAA TGT TTG AGC TCA AGG AGA TGC CAC CTT GTC   2,360
      761 Ser Tyr Trp Thr Gly Ser Ile Ser Pro Lys Cys Leu Ser Ser Arg Arg Cys His Leu Val

GGG GAA TGC CAT GTG AAT AGG TGT CTG TCT TGG AGG GAC AAT GAA ACT TCA GCA GAG TTT   2,420
      781 Gly Glu Cys His Val Asn Arg Cys Leu Ser Trp Arg Asp Asn Glu Thr Ser Ala Glu Phe

TCA TTT GTT GGG GAA AGC ACG ACC ATG CGA GAG AAT AAG TGT TTT GAG CAA TGT GGA GGA   2,480
      801 Ser Phe Val Gly Glu Ser Thr Thr Met Arg Glu Asn Lys Cys Phe Glu Gln Cys Gly Gly
                                                                                    Pst I
          TGG GGG TGT GGG TGT TTC AAT GTG AAC CCA TCT TGC TTA TTT GTG CAC ACG TAT CTG CAG   2,540
      821 Trp Gly Cys Gly Cys Phe Asn Val Asn Pro Ser Cys Leu Phe Val His Thr Tyr Leu Gln
                                                                                    Xba I
          TCA GTT AGA AAA GAG GCC CTT AGA GTT TTT AAC TGT ATC GAC TGG GTG CAT AAA CTC ACT   2,600
      841 Ser Val Arg Lys Glu Ala Leu Arg Val Phe Asn Cys Ile Asp Trp Val His Lys Leu Thr
```

FIG. 2c

```
          CTA GAG ATC ACA GAC TTT GAT GGC TCT GTT TCA ACA ATA GAC TTG GGA GCA TCA TCT AGC  2,660
      861 Leu Glu Ile Thr Asp Phe Asp Gly Ser Val Ser Thr Ile Asp Leu Gly Ala Ser Ser Ser
          CGT TTC ACA AAC TGG GGT TCA GTT AGC CTC TCA CTG GAC GCA GAG GGC ATC TCA GGC TCA  2,720
      881 Arg Phe Thr Asn Trp Gly Ser Val Ser Leu Ser Leu Asp Ala Glu Gly Ile Ser Gly Ser
          AAT AGC TTT TCT TTC ATT GAG AGC CCA AGC AAA GGG TAT GCA ATT GTT GAT GAG CCA TCC  2,780
      901 Asn Ser Phe Ser Phe Ile Glu Ser Pro Ser Lys Gly Tyr Ala Ile Val Asp Glu Pro Ser
          TCA GAA ATT CCT CGG CAA GGG TTC TTG GGG GAG ATC AGG TGC AAT TCA GAG TCC TCA GTC  2,840
      921 Ser Glu Ile Pro Arg Gln Gly Phe Leu Gly Glu Ile Arg Cys Asn Ser Glu Ser Ser Val
          CTG AGT GCT CAT GAA TCA TGC CTT AGG GCA CCA AAC CTT ATC TCA TAC AAG CCC ATG ATA  2,900
      941 Leu Ser Ala His Glu Ser Cys Leu Arg Ala Pro Asn Leu Ile Ser Tyr Lys Pro Met Ile
          GAT CAA TTG GAG TGC ACA ACA AAT CTG ATT GAT CCC TTT GTT GTC TTT GAG AGG GGT TCT  2,960
      961 Asp Gln Leu Glu Cys Thr Thr Asn Leu Ile Asp Pro Phe Val Val Phe Glu Arg Gly Ser
          CTG CCA CAG ACA AGG AAT GAT AAA ACC TTT GCA GCT TCA AAA GGA AAT AGA GGT GTT CAA  3,020
      981 Leu Pro Gln Thr Arg Asn Asp Lys Thr Phe Ala Ala Ser Lys Gly Asn Arg Gly Val Gln
              Hind III
          GCT TTC TCT AAG GGC TCT GTA CAA GCT GAT CTA ACT CTG ATG TTT GAC AAT TTT GAG GTG  3,080
    1,001 Ala Phe Ser Lys Gly Ser Val Gln Ala Asp Leu Thr Leu Met Phe Asp Asn Phe Glu Val
          GAC TTT GTG GGA GCA GCC GTA TCT TGT GAT GCC GCC TTC TTA AAT TTG ACA GGT GCA TAT  3,140
    1,021 Asp Phe Val Gly Ala Ala Val Ser Cys Asp Ala Ala Phe Leu Asn Leu Thr Gly Ala Tyr
          TCT TGC AAT GCA GGG GCC AGG GTC TGC CTG TCT ATC ACA TCC ACA GGA ACT GGA TCT CTC  3,200
    1,041 Ser Cys Asn Ala Gly Ala Arg Val Cys Leu Ser Ile Thr Ser Thr Gly Thr Gly Ser Leu
          TCT GCC CAC AAT AAG GAT GGG TCT CTG CAT ATA GTC CTT CCA TCA GAG AAT GGA ACA AAA  3,260
    1,061 Ser Ala His Asn Lys Asp Gly Ser Leu His Ile Val Leu Pro Ser Glu Asn Gly Thr Lys
          GAC CAG TGT CAG ATA CTA CAC TTC ACT GTG CCT GAA GTA GAG GAG GAG TTT ATG TAC TCT  3,320
    1,081 Asp Gln Cys Gln Ile Leu His Phe Thr Val Pro Glu Val Glu Glu Glu Phe Met Tyr Ser
          TGT GAT GGA GAT GAG CGG CCT CTG TTG GTG AAG GGG ACC CTG ATA GCC ATT GAT CCA TTT  3,380
    1,101 Cys Asp Gly Asp Glu Arg Pro Leu Leu Val Lys Gly Thr Leu Ile Ala Ile Asp Pro Phe
          GAT GAT AGG CGG GAA GCA GGG GGG GAA TCA ACA GTT GTG AAT CCA AAA TCT GGA TCT TGG  3,440
    1,121 Asp Asp Arg Arg Glu Ala Gly Gly Glu Ser Thr Val Val Asn Pro Lys Ser Gly Ser Trp
          AAT TTC TTT GAC TGG TTT TCT GGA CTC ATG AGT TGG TTT GGA GGG CCT CTT AAA CTA TAC  3,500
    1,141 Asn Phe Phe Asp Trp Phe Ser Gly Leu Met Ser Trp Phe Gly Gly Pro Leu Lys Leu Tyr
          TCC TCA TTT GCC TGT ATG TTG CAT TAT CAA TTG GGC TCT TTT TCC TCC TTA TAT ATC TTG  3,560
    1,161 Ser Ser Phe Ala Cys Met Leu His Tyr Gln Leu Gly Ser Phe Ser Ser Leu Tyr Ile Leu
                  Stu I
          GAA GAA CAG GCC TCT CTA AAA TGT GGC TTG CTG CCA CTA AGA AGG CCT CAT AGA TCA GTA  3,620
    1,181 Glu Glu Gln Ala Ser Leu Lys Cys Gly Leu Leu Pro Leu Arg Arg Pro His Arg Ser Val
          CGT GTA AAA GTA ATA TGT TGA AAT AAG TAG ACA CAA GCA AAC CTA ATT ATG TAA GTG TTG  3,680
    1,201 Arg Val Lys Val Ile Cys *** Asn Lys *** Thr Gln Ala Asn Leu Ile Met *** Val Leu
          TAC AGA TAG GTC AAA TTA TTG GAA TAT CCA AGC TTA GAA ACT TAT GCA ATA ATA CTT TAG  3,740
    1,221 Tyr Arg *** Val Lys Leu Leu Glu Tyr Pro Ser Leu Glu Thr Tyr Ala Ile Ile Leu ***
          ATG TAA GCT TAG TTG TAA TTT GGG GTG GTG GGG TGA GGC AGC AGC AGT CTC AAG TGC TTG  3,800
    1,241 Met *** Ala *** Leu *** Phe Gly Val Val Gly *** Gly Ser Ser Ser Leu Lys Cys Leu
          TGA ATA TTC TAG TTG GCG TAA TCG TCT TTT GCC AGA TTA GCT GGG AAT TAA ACT AAC TCT  3,860
    1,261 *** Ile Phe *** Leu Ala *** Ser Ser Phe Ala Arg Leu Ala Gly Asn *** Thr Asn Ser
          TTG AAG TTG CAC CGG TCT TTG TGT                                                   3,920
    1,281 Leu Lys Leu His Arg Ser Leu Cys
```

FIG. 4
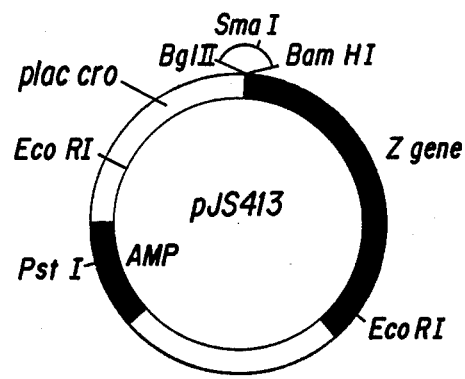
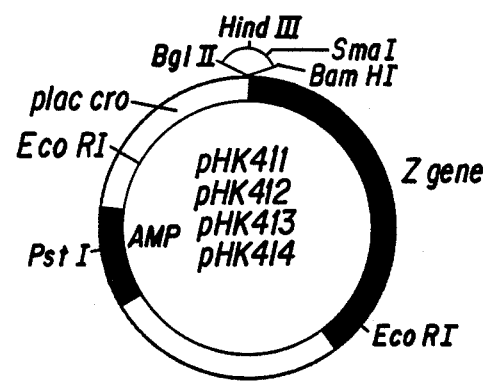
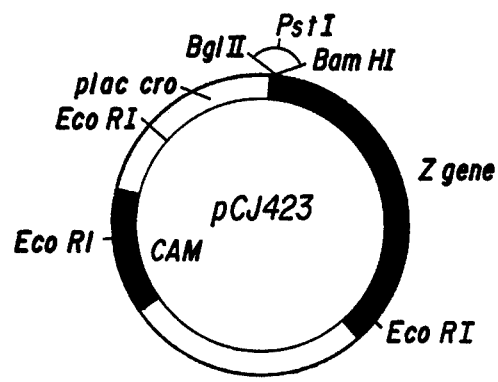

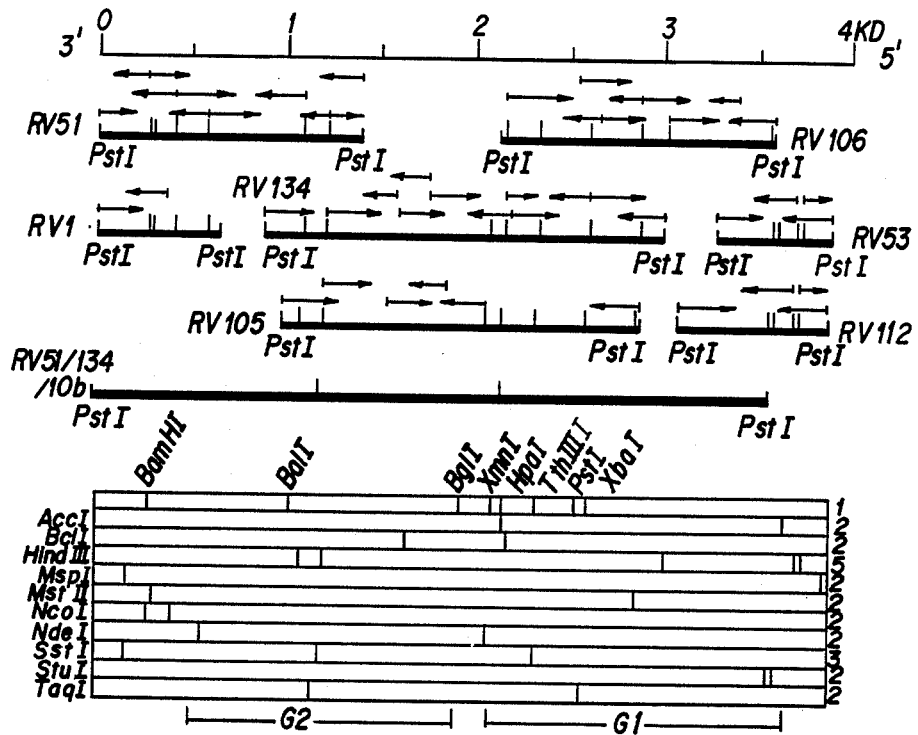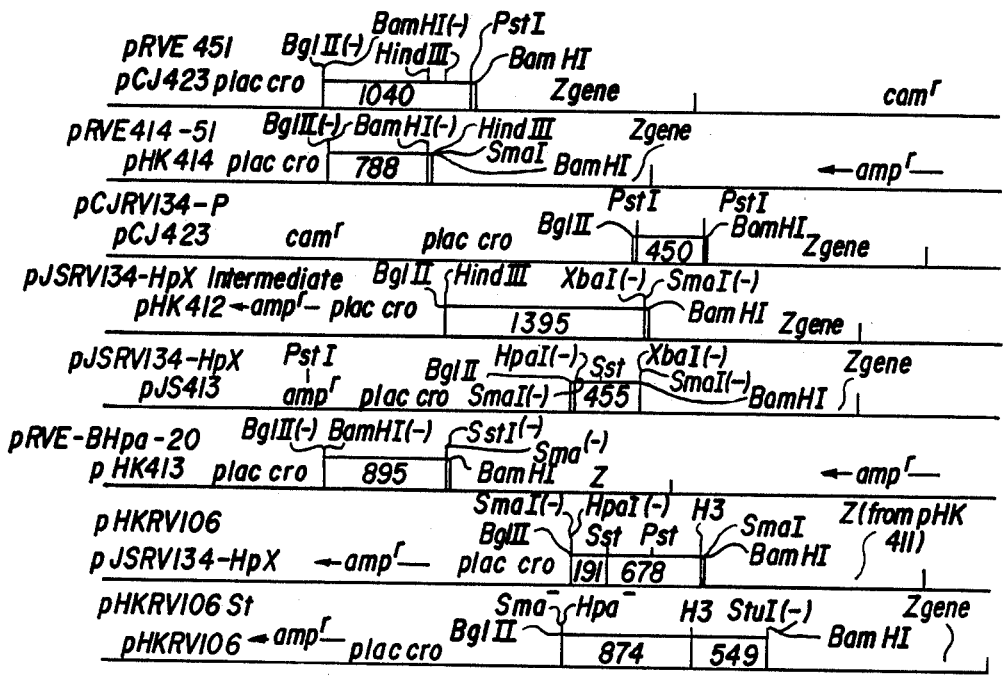
FIG. 5

VACCINES AGAINST RIFT VALLEY FEVER VIRUS

The present application is a continuation-in-part of application Ser. No. 530,887 filed Sept. 9, 1983, abandoned, which is herein incorporated by reference.

TABLE OF CONTENTS

1. Field of the Invention
2. Background of the Invention
   2.1. Recombinant DNA Technology and Gene Expression
   2.2. Vaccines
   2.3. Rift Valley Fever
   2.4. Rift Valley Fever Virus
3. Summary of the Invention
4. Brief Description of the Figures
5. Detailed Description of the Invention
   5.1. Isolation and Cloning of RVFV Genomic RNA
   5.1.2. Synthesis of cDNA
   5.1.3. Preparation of Double-Stranded DNA
   5.1.4. Insertion of the RVFV Sequence Into a Cloning Vector
   5.1.5. Selection of Transformants Carrying RVFV cDNA Sequences
   5.2. Insertion of the RVFV Gene into an Expression Vector
   5.3. Preparation of Fusion Proteins
   5.4. Preparation of Unfused Protein
      5.4.1. Co-Transformation of Host Cells
      5.4.2. Transformation of Host Cells With One Plasmid Carrying Two Genes
      5.4.3. Modification of the Fusion Protein Gene
   5.5. Characterization of the Gene Product
   5.6. Purification of the Gene Product
   5.7. Formulation of a Vaccine
6. Example
   6.1. General Procedures Used for Preparation of the Plasmids
      6.1.1. Plasmid DNA Isolation
      6.1.2. Conditions for Restriction Enzyme Digestions
      6.1.3. Restriction Enzyme Buffers
      6.1.4. Modification of DNA
      6.1.5. Gel Purification of DNA Fragments
      6.1.6. DNA Ligation
   6.2. Isolation and Molecular Cloning of The RVFV Genome
      6.2.1. Isolation of RVFV Genomic RNA
      6.2.2. Preparation of cDNA from Genomic RVFV RNA
      6.2.3. Insertion of RVFV cDNA Into Cloning Vectors
      6.2.4. Identification of Bacterial Colonies Containing RVFV Sequences Derived from the M RNA
      6.2.5. Restriction Mapping and DNA Sequencing of RVFV MRNA
      6.2.6. Construction of pRV51/134/106
   6.3. Expression Cloning of RVFV Gene Sequences Derived from the Viral M RNA
      6.3.1. Expression Vectors Containing the lac Promoter: pHK414, pHK412, pHK411, pJS413 and pCJ423
      6.3.2. Insertion of RVFV DNA Sequences Derived from the M RNA into the lac Promoter Expression Vectors
      6.3.3. Expression Vectors Containing the tac Promoter: ptc412, ptc413 and ptc414
      6.3.4. Insertion of RVFV DNA sequences Derived from the M RNA into the tac Promoter Expression Vectors
      6.3.5. Identification of Transformants that Express RVFV Genetic Sequences as Protein
   6.4. Immunologic Characterization of the RVFV-Related Proteins Expressed in E. coli
      6.4.1. Antigenicity of RVFV-Related Proteins Expressed in E. coli
      6.4.2. Immunogenicity of RVFV-Related Proteins Expressed in E. coli
7. Deposit of Microorganisms

1. FIELD OF THE INVENTION

This invention is directed to processes for the production of proteins related to the glycoproteins of Rift Valley Fever Virus (RVFV), and to processes and compositions for making and using novel DNA sequences, plasmids and microorganisms (both eucaryotic and procaryotic) to produce such proteins.

This invention further relates to the use of recombinant DNA techniques to produce RVFV polypeptides which can be used as immunogens in vaccine formulations and/or in diagnostic assays for RFVF. DNA sequences coding for the glycoproteins of RVFV, or a portion thereof, are inserted into a DNA vector, such as viral DNA, plasmid DNA or bacteriophage DNA, such that the vector is capable of replicating and directing expression of the glycoprotein gene in a bacterial host or other single cell system. The resulting recombinant DNA molecule is introduced into host cells to enable production of the desired protein, or a portion or of molecular variant thereof, by the host cells. Since antisera directed against RVFV glycoproteins are capable of neutralizing the virus, the microbially produced protein could be used as an immunogen in a vaccine formulation to protect humans or animals against RVFV infection.

The present invention also provides a method of producing RVFV antigens of general importance in human and veterinary medicine and in microbiological research. This includes use of the RVFV proteins produced by the present invention as highly preproducible standard antigens for ultrasensitive assays such as radioimmunoassays. These antigens may also be used as a diagnostic tool for detection of antibodies to RVFV in biological samples. Finally, the RVFV proteins produced by the present invention will be invaluable in elucidating the mechanisms of replicating and pathogenesis of the various isolates of Rift Valley Fever Virus.

2. BACKGROUND OF THE INVENTION

2.1. Recombinant DNA Technology and Gene Expression

Recombinant DNA technology involves insertion of specific DNA sequences into a DNA vehicle (vector) to form a chimeric DNA molecule which is capable of replication in a host cell. Generally, the inserted DNA sequence is foreign to the recipient host, i.e., the inserted DNA sequence and the DNA vector are derived from organisms which do not exchange genetic information in nature, or the inserted DNA sequence may be wholly or partially synthetically made. In recent years several general methods have been developed which enable construction of recombinant DNA molecules. For example, U.S. Pat. No. 4,237,224 to Cohen and Boyer describes production of such recombinant plasmids using restriction enzymes and methods known as ligation. These recombinant plasmids are then introduced and replicated in unicellular organisms by means of transformation. Because of the general applicability of the techniques described therein, U.S. Pat. No. 4,237,224 is hereby incorporated by reference into the present specification.

Another method for introducing recombinant DNA molecules into unicellular organisms is described by Collins and Hohn in U.S. Pat. No. 4,304,863 which is also incorporated herein by reference. This method utilizes a packaging/transduction system with bacteriophage vectors (cosmids).

Regardless of the method used for construction, the recombinant DNA molecule must be compatible with the host cell, i.e., capable of autonomous replication in the host cell. The recombinant DNA molecule should also have a marker function which allows the selection of host cells so transformed by the recombinant DNA molecule. In addition, if all of the proper replication, transcription and translation signals are correctly arranged on the chimeric DNA molecule, the foreign gene will be expressed in the transformed cells and their progeny.

As is characteristic of all viruses which infect eucaryotic cells, RVFV requires a eucaryotic host cell system in which to replicate its genome, express its viral genes and generate its progeny. The signals and control elements for DNA replication, gene expression and virus assembly in eucaryotes differ from those of procaryotes. This is of critical importance when attempts are made to express in procaryotic host cells in a gene which is naturally expressed only in eucaryotic cells.

These different genetic signals and processing events control many levels of gene expression, i.e., DNA transcription and messenger RNA translation. Transcription of DNA is dependent upon the presence of a promoter which is a DNA sequence that directs the binding of RNA polymerase and thereby promotes transcription. The DNA sequences of eucaryotic promoters differ from those of procaryotic promoters. Furthermore, eucaryotic promoters and accompanying genetic signals may not be recognized in or may not function in a procaryotic system.

Similarly, translation of messenger RNA (mRNA) in procaryotes depends upon the presence of the proper procarytic signals which differ from those of eucaryotes. Efficient translation of mRNA in procaryotes requires a ribosome binding site called the Shine Dalgarno (SD) sequence on the mRNA. This sequence is a short nucleotide sequence of mRNA that is located before the start codon (AUG) which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome (Roberts and Lauer, 1979, Methods in Enzymology, 68: 473).

Many factors complicate the expression of eucaryotic genes in procaryotes even after the proper signals are inserted and appropriately positioned. A clear understanding of the nature of these factors and the mechanisms by which they operate is presently lacking. One such factor is the presence of an active proteolytic system in E. coli and other bacteria. This protein-degrading system appears to selectively destroy "abnormal" or foreign proteins such as eucaryotic proteins. A tremendous utility, therefore, would be afforded by the development of a means to protect eucaryotic proteins expressed in bacteria from proteolytic degradation. One strategy is to construct hybrid genes in which the eucaryotic sequence is ligated in phase (i.e., in the correct translational reading frame) with a procaryotic gene. Host cell expression of the hybrid gene results in a fusion protein product (a protein that is a hybrid of procaryotic and foreign or eucaryotic amino acid sequences).

Construction of hybrid genes was the approach used in the molecular cloning of genes encoding a number of eucaryotic proteins, such as somatostatin, rat proinsulin, growth hormone, and ovalbumin-like protein. Although the molecular cloning and expression of several eucaryotic genes has been accomplished, this has not heretofore been done for the glycoprotein genes of RVFV. Nor is the state of the art such that expression of foreign or eucaryotic genes in procaryotic host cells may be routinely performed.

2.2. Vaccines

There are four basic approaches to the prevention and/or treatment of viral infections: (1) vaccines that elicit an active immune response; (2) chemotherapeutic agents that inhibit viral replication; (3) agents that induce the synthesis of interferon; and (4) administration of antibodies for passive immunity. All four can be used to prevent infection, but are more effective when applied early in infection. Vaccination, or active immunization is usually ineffective after infection has begun.

Viruses are small and relatively simple in structure. Viruses contain a central core of nucleic acid (either DNA or RNA) surrounded by a protein coat called a capsid. In many viruses, the capsid is surrounded by a loose membranous envelope which is similar to a cellular membrane in composition. Nonenveloped viruses are referred to as naked capsids. The nucleic acid core of viruses contains, through a complex coding scheme, the information needed for infecting cells of host tissues, replicating the virus genome and producing the protein components of the virion particle.

When an animal is infected by a virus, it reacts to the capsid or envelope protein as a foreign protein. The host may develop immunity, which is manifested by the formation of antibodies and lymphocytes which are capable of recognizing the viral proteins. This may result in inactivation of the virus and lysis of infected cells. Thus, conventional vaccines providing active immunity are usually prepared by producing large amounts of virus in cell tissue culture or in laboratory animals and then rendering the virus harmless without destroying its immunological properties.

Traditionally, this is accomplished either by inactivating the infectivity of the virus (i.e., "killing" the virus, usually by treatment with various chemical agents such as formaldehyde) for use in inactivated vaccines, or by selecting an avirulent or attenuated (modified) virus for use in live vaccines (attenuated vaccines). Attenuation is often established by adapting the virus to unusual growth conditions (i.e., different animals hosts or cell cultures) and by frequent passage in cell culture of large viral inocula to select mutants which have lost virulence and thus produce minor or no clinical symptoms. A few vaccines still used in veterinary practice consist of fully virulent, infectious virus injected in a site where viral multiplication is of little consequence. This procedure has been considered too dangerous for use in man.

Attenuated virus vaccines are generally excellent immunogens because the attenuated virus multiplies in the host thereby eliciting long-lasting immunity. Attenuated vaccines induce humoral antibodies directed against all viral antigens, both surface and internal antigens of the virion. However, a number of problems are encountered with the use of live vaccines, such as insufficient attenuation of the virus, genetic instability of the virus, contamination by adventitious viruses in cell cultures used to grow the vaccine virus, and, finally, instability of the vaccine (e.g., heat-lability).

While the use of inactivated vaccines (employing "killed" or inactivated virus that does not multiply) avoids the difficulties encountered with the use of live vaccines, killed viruses do not multiply in the immunized animal and usually produce antibodies directed against only virion structural components. There are two major difficulties with inactivated vaccines. Firstly, it is frequently not possible to inactivate all the virus particles. Secondly, there is the difficulty of producing enough virus to provide the necessary quantity of the relevant antigen. Other difficulties encountered with the use of inactivated vaccines are that the immunity achieved is brief and often requires additional immunizations (boosters), the antigenic sites on the viral proteins may be altered by the inactivating chemical treatment, and thus be less immunogenic or may induce antibodies that are less effective at neutralizing viral infections, and that these vaccines do not induce satisfactory levels of secretory antibody.

Subunit vaccines contain only the necessary and relevant immunogenic material, such as the capsid proteins of nonenveloped icosahedral viruses or the peplomers (glycoprotein spikes) of enveloped viruses. Subunit vaccines can be made by isolating the relevant subunit from highly purified viral fractions, or by synthesizing the relevant polypeptide. A major advantage of subunit vaccines is the exclusion of genetic material of viral origin and of host- or donor-derived interfering substances. However, at present, production of subunit vaccines using these methods is too expensive for widespread commercial use. Recombinant DNA technology has much to offer in the production of subunit vaccines; the molecular cloning and host cell expression of viral genes which encode the relevant immunogenic portions of the virus or its proteins can produce sufficient quantities of the relevant immunogen for use in a subunit vaccine.

Vaccines are often administered in an emulsion with various adjuvants. Adjuvants aid in attaining a more durable and higher level of immunity using smaller amounts of antigen in fewer doses than if the immunogen were administered alone. The mechanism of adjuvant action is complex and not completely understood. However, it may involve the stimulation of phagocytosis and other activities of the reticuloendothelial system as well as a delayed release and degradation of the antigen.

2.3. Rift Valley Fever

Rift Valley Fever is an arthropod-borne viral disease primarily affecting cloven-hoofed animals but with increasing human involvement. Since the initial isolation of the virus from a newborn lamb during a 1930 epizootic in Kenya, periodic outbreaks have occurred in many ecologically diverse areas of sub-Saharan Africa. The virus has an unusually wide range of vertebrate and invertebrate hosts which function together to amplify and spread the virus during epizootics, and perhaps maintain it during enzootic periods. The disease predominantly affects ruminants causing abortions in adult animals and high mortality in young offspring. Cattle and sheep are the most susceptible to RVFV, and symptoms include anorexia, salivation, blood stained nasal discharge and fetid diarrhea. Mortality rarely exceeds 10% in adult animals but has been documented as high as 70% among infected calves and 90% among infected lambs (Easterday, 1965, Adv. Vet. Sci. 10: 65-217).

Human disease occurring during most epizootics was described as a non-fatal febrile illness usually involving field and laboratory investigators, farmers, and animal handlers. However, in 1977 and again in 1978, extensive RVFV epizootics occurred in several areas of the Nile Delta and Valley in Egypt, during which occurred unprecedented human disease with severe clinical manifestations and heavy mortality. During that outbreak, the disease presented four distinct clinical syndromes in humans: (1) The most common syndrome was uncomplicated Rift Valley Fever (RVF) where patients experienced sudden onset of fever and malaise with an initial rigor, headaches and lower back myalgia. (2) A second clinical syndrome was RVF with ocular complcations. These complications included acute febrile illness followed by a decrease in visual acuity over a period of one to two weeks. Approximately half of the patients with more severe macular lesions had permanent loss of central vision. (3) A third syndrome included an apparent increase in abortions among infected women. (4) The most serious syndrome was hemorrhagic RVF. Patients experienced the usual sudden onset of febrile illness but 2-4 days later developed jaundice and hemorrhagic manifestations. In one study, 9 of 29 patients with hemorrhagic illness died (Daubney, et al., 1939, J. Path. Bact. 34: 545-579).

The 1977-78 outbreak of RVF with its serious human involvement has spurred research into treatment and prevention of the disease. Currently used animal vaccines include a live attenuated vaccine and an inactivated vaccine. However, these vaccines have serious shortcomings. The live vaccine induces abortions and may not efficiently immunize all species of domestic animals, while the inactivated vaccine needs frequent boosting to be effective. A killed-virus human vaccine has been developed by the U.S. Army by culturing the virus in monkey cells, but it is only available in limited supply and requires multiple doses for immunization (Findley, 1932 Trans. R. Sc. Trop. Med. Hyg. 25: 229-265).

2.4. Rift Valley Fever Virus

The Rift Valley Fever virus is a member of the relatively recently defined family of arthropod-borne viruses known as Bunyaviridae. Serological evidence has shown that RVFV is related to members of the phlebotomus fever virus serogroup. These viruses are spherical particles 90-100 nm in diameter and possess envelopes containing glycoproteins. The virus has a single-stranded, three segment, negative sense RNA genome with a total molecular weight of approximately 4 to $6 \times 10^6$ daltons. The viral RNA segments are designated according to their sizes: large (L, approximately $2.7 \times 10^6$ daltons) presumably coding for the viral polymerase/replicase; medium (M, approximately $1.7 \times 10^6$ daltons) coding for the viral glycoproteins; and small (S, approximately $0.6 \times 10^6$ daltons) coding for the nucleocapsid protein and possibly a nonstructural protein.

The capsid consists of a nucleocapsid protein (N), and a single RNA type (L, M, or S). The RNA species have free 5' and 3' ends but can be extracted from nucleocapsids (or virus particles) as noncovalently closed circles. Two virus-specific glycoproteins (designated G1 and G2) have been identified in all bunyaviruses so far analyzed, and are located on the outer surface of the virus particles.

Virus replication occurs in the cytoplasm of the infected cells. Virus particles are formed by budding primarily into the Golgi cisternae. The virions are liberated from the infected cell by fusion of the intracellular vacuoles with the cellular plasma membrane and virus egestion, or by cellular destruction and discharge of the cell contents (Weiss, 1957, Full. Epizoot. Dis Afr. 5: 431–458).

3. SUMMARY OF THE INVENTION

Methods and compositions are provided for the cloning and expression (as proteins) of RVFV genetic sequences in single-cell host organisms. Also described are methods for culturing these novel single-cell organisms to produce the RVFV gene products and methods for the purification of the gene products. The RVFV-related proteins produced by the recombinant DNA techniques described herein may be formulated for use as immunogens in vaccines to protect humans or animals against RVFV infection.

Briefly, the RVFV RNA genome was isolated from viral particles and complementary DNA (cDNA) was synthesized using the RVFV M RNA as template. The cDNA was subsequently inserted into plasmid vectors to form recombinant plasmids which serve as biologically functional replication units. These recombinant plasmids were constructed so as to facilitate both the replication and expression of RVFV genes upon transformation of compatible host cells. Additionally, the plasmids provided for a one-step identification of transformed microorganisms actively expressing RVFV genes. Finally, methods are described for isolating and expressing the gene products and for formulating a vaccine.

The proteins thus produced may be used in vaccine formulations. Vaccines produced by recombinant DNA technology can address many of the problems involved in the production of conventional vaccines. First, very little virus is needed in order to isolate the relevant genetic sequences which are used in the construction of recombinant DNA molecules. The use of such recombinant molecules to transform appropriate host cells allows for the production of effective vaccines against viruses that cannot be grown in cell tissue culture or in laboratory animals. Second, recombinant DNA vaccines are a type of subunit vaccine, they contain no viral genetic material or toxic, contaminating host substances. Third, since large scale bacterial fermentation can be used, the vaccines can be produced economically in large quantities.

4. BRIEF DESCRIPTION OF THE FIGURES

The present invention may be more fully understood by reference to the following detailed description of the invention, examples of specific embodiments of the invention, and the appended figures in which:

FIG. 1 represents a restriction endonuclease map of the RVFV cDNA inserts of pRV1, pRV51, pRV53, pRV105, pRV106, pRV112, pRV134, and pRV51/134/106 as aligned with the viral genomic M RNA (in a 3' to 5' orientation). The RVFV restriction sites are indicated by long vertical lines. The RVFV DNA insert of each cDNA clone depicted possesses PstI restriction sites which are indicated by short vertical lines. In addition, the sequencing strategy is indicated by horizontal arrows. FIGS. 2a–c represent the complete DNA sequence corresponding to the M MRVF RNA. The DNA sequence is reported in the positive reading frame along with its deduced amino acid sequence.

FIG. 3A represents an analysis of all possible reading frames of both the positive and negative polarities within the M RVFV sequence. The positions of the stop codons (UGA, UAG, and UAA codons) are indicated by vertical lines.

FIG. 3B represents the molecular organization of the viral M RNA segment of RVFV, and the complement to viral M RNA showing the major open reading frame and alignment of mature glycoprotein coding regions, G2 and G1. The "⍟" indicates potential glycosylation sites on the protein. BH, C12 and 106S represent regions of the RVFV M RNA segment that are expressed by some transformants described herein. The percentages indicate the proportion of the mature protein represented by each of the three sequences.

FIG. 4 (not drawn to scale) represents the construction of the lac promoter expression vectors pJS413, pHK414, pHK412, pHK413, pHK411 and pCJ423.

FIG. 5 (not drawn to scale) represents the construction of various recombinant plasmids derived from portions of the RVFV M nucleotide sequence and the E. coli lac promoter expression vectors.

Figure 8:
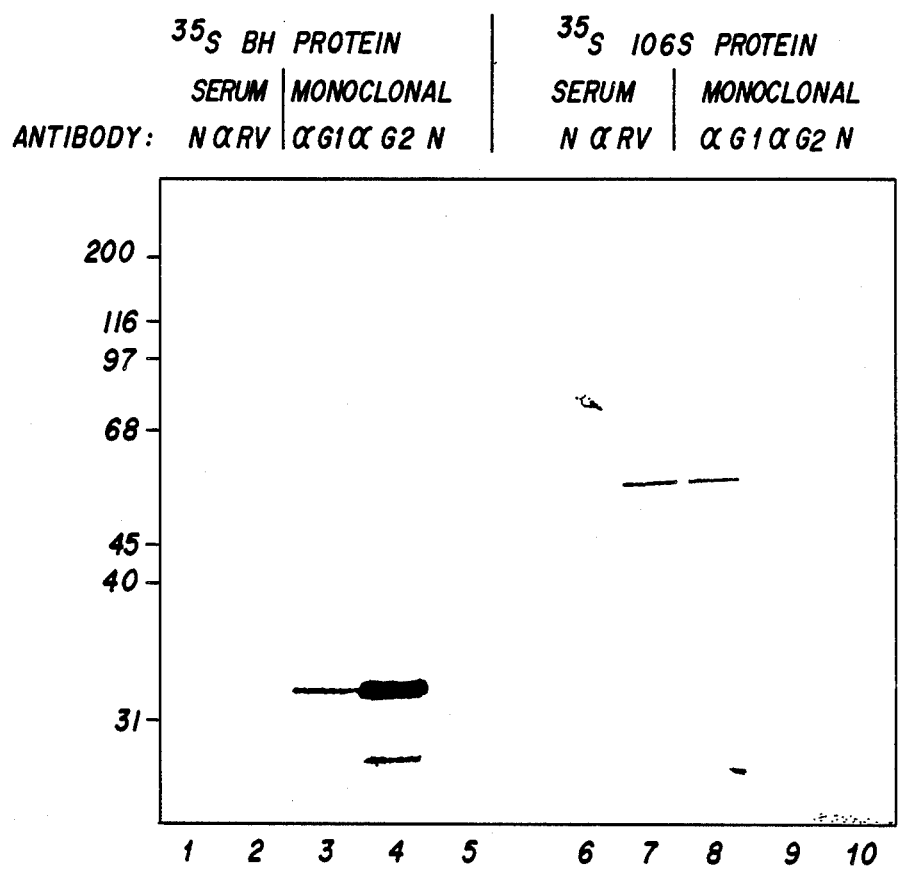

FIG. 8 represents a fluorogram of an SDS-polyacrylamide gel in which [$^{35}$S]-methionine-labeled immunoprecipitated proteins have been electrophoresed. E. coli transformants containing either of the RVFV expression plasmids, ptRV-BH or ptRV-106S, were grown in the presence of inducer (1mM IPTG) and [$^{35}$S]-methionine. The bacterial cells were then disrupted and aliquots of a cell-free lysate from each transformant were immunoprecipitated with: normal guinea pig serum (lanes 1 and 6); guinea pig serum from an animal hyperimmunized with whole RVFV (lanes 2 and 7); a monoclonal antibody specific for glycoprotein G1 (lanes 3 and 8); a monoclonal antibody specific for glycoprotein G2 (lanes 4 and 9); a monoclonal antibody specific for a protein unrelated to RVFV proteins (lanes 5 and 10). Lanes 1 through 5 represent the ptRV-BH transformant lysate and lanes 6 through 10 represent the ptRV-106S transformant lysate.

5. DETAILED DESCRIPTION OF THE INVENTION

The method of this invention may be divided into the following stages for the purpose of description: (a) identification and isolation of the RVFV RNA gene or gene fragment; (b) preparation of cDNA from portions of the single-stranded RVFV RNA genome; (c) amplification of the cDNA by its insertion into DNA plasmid and propagation in single-cell hosts (i.e., molecular cloning); (d) insertion of the cDNA gene or gene fragment into a cloning expression vector to form a recombinant DNA molecule which is used to transform a single-cell organism, (e) identification and growth of the transformants which are capable of replicating and expressing the gene; (f) determination of the immunopotency of the gene product by assessment of its ability to elicit the production of antibodies directed against RVFV (including virus neutralizing anitbodies); and (g) formulation and use of subunit vaccines. For purposes of clarity, the method will be discussed in terms of the M RNA encoded glycoprotein gene. The same techniques, however, may be applied in an analogous fashion to similarly produce a polypeptide related to any of the RVFV proteins.

5.1 Isolation and Cloning of RVFV Genomic RNA

RVFV particles can be isolated from serum samples, collected from animals (including, but not limited to, mammals, marsupials, birds, rodents, or man) infected with any strain of RVFV. The virus may also be isolated from an arthropod carrier (e.g., mosquitos, sandflies, etc.). The virus can be propagated by growing RVFV in cells in tissue culture (e.g., BHK cells, Vero cells, etc.) and the L, M, and S nucleocapsids can be purified from the cultured cells by standard techniques such as centrifugation, gradient sedimentation, etc. The viral RNA species may be obtained from purified nucleocapsids by extraction with phenol or with SDS (sodium dodecyl sulfate) and phenol, etc.

In order to provide a continuous supply of large amounts of RVFV genomic sequences it is desirable to amplify the sequences by molecular cloning. Once the RNA species are isolated, they may be converted into a complementary DNA molecule (cDNA) that can be inserted into a cloning vector which is then used to transform appropriate host cells. Alternatively, the purified RVFV RNA can be inserted directly into DNA cloning vectors using techniques described in U.S. patent application Ser. No. 491,099 filed May 3, 1983 by Kempe et al. which is hereby incorporated by reference. In either case, amplification of the RVFV sequences occurs during growth of transformants. Alternatives to isolating RVFV RNA from virus as starting material include but are not limited to chemically synthesizing the RVFV sequence itself or isolating RVFV sequences from recombinant plasmids.

5.1.2. Synthesis of cDNA

A particularly used approach for the synthesis of RVFV cDNA is to first attach a series of adenine residues to the 3' end of the RNA molecule. This may be done by treating RVFV RNA with *E. coli* poly(A) polymerase and adenosine triphosphate. Poly(A) polymerase readily polymerizes the AMP of ATP onto the free 3' terminal hydroxyl group of RNA. The length of poly(A) synthesized varies from 300 bases to several thousand bases. Unlike polynucleotide phosphorylase, this enzyme does not catalyze the phosphorolysis of poly(A) and shows no primer-independent activity (Bethesda Research Laboratories, Inc., Gaithersburg, MD). The resulting poly(A)-tailed RNA is then partially purified by passing the reaction solution over an oligo(dT)-cellulose column which binds only the RNA that has the poly(A) 3' end. The bound poly(A) RNA is then released by washing the column with sodium chloride-free loading buffer.

The poly(A) RNA can then be enzymatically converted to cDNA using the enzyme RNA-dependent DNA polymerase (reverse transcriptase). Reverse transcriptase is used chiefly to transcribe RNA into DNA, which can then be inserted into DNA vectors. When the RNA molecule has a poly(A) tail, the primer used for this reaction can be oligo(dT). However, a collection of randomly generated oligodeoxynucleotides may be used to prime cDNA systhesis on any single-stranded RNA template. If randomly generated oligodeoxynucleotides are used as primers, the diversity of these molecules must be so large as to guarantee that some of them will be complementary to sequences in the template nucleic acid. Because different oligonucleotides bind to different sequences in the template, all parts of the template will be represented in the resulting cDNA at equal frequency. By contrast, oligo(dT) binds only to poly(A) located by the 3' end of the RNA molecule (or to any poly(A) stretches within the molecule), and therefore specifically primes the synthesis of cDNA from the 3' end of the mRNA template.

Treatment of the poly(A) RNA with reverse transcriptase and an oligo (dT) primer results in a RNA/cDNA hybrid which must be separated (or the RNA strand destroyed) in order to retrieve the single-stranded cDNA molecule representing the RVFV sequences be cloned. The removal of RNA may be accomplished by treatment with hot alkali or with ribonuclease which will hydrolyze or digest the RNA component; the resulting cDNA is a single-stranded DNA molecule (containing a hairpin loop of single-stranded DNA at the 3' end) which is then isolated from the reaction mixture using standard techniques such as rate zonal sedimentation, electrophoresis, chromatography, etc.

5.1.3. Preparation of Double-Stranded DNA

The single-stranded DNA may be converted to double-stranded DNA (dsDNA) by treating the cDNA species with *E. coli* DNA polymerase I. The reaction may be carried out at pH 6.9 to minimize the 5' to 3' exonuclease activity of DNA polymerase I and at 15° C. to minimize the possibility of synthesizing "snap back" DNA. The Klenow fragment of DNA polymerase I may also be successfully employed to synthesize the second cDNA strand. The Klenow fragment enzyme consists of a single polypeptide chain produced by cleavage of intact DNA polymerase I with the proteolytic enzyme subtilisin. This peptide carries the 5' to 3' polymerase activity and the 3' to 5' exonuclease activity of intact DNA polymerase I but lacks the 5' to 3' exonuclease activity. Reverse transcriptase may also be utilized to synthesize the second cDNA strand using conditions similar to those already described for the synthesis of first cDNA strand. In either case, the hairpin loop of the cDNA may serve to prime the reaction. Both DNA polymerase I and reverse transcriptase may be used together in the conversion of single-stranded to double-stranded DNA (Erasmus, and Coetzer, 1981 Contri. Epidem. Biostatist. 3: 77–82, Karger, Basel).

After synthesis of dsDNA is complete, the first and second strands remain covalently joined by the hairpin loop that was used to prime the second strand synthesis (Meegan, Watten and Laughlin, 1981, Clinical Experience with Rift Valley Fever in Humans During the 1977 Egyptian Epizootic, Contri, Epidem. Biostatist. 3: 77–82, Karger, Basel). This single-stranded loop is susceptible to cleavage by the single-strand-specific nuclease, S1. However, the resulting termini are not always perfectly blunt-ended, and the efficiency of subsequent cloning can be improved if the ends are "filled in" with the Klenow fragment of E. coli DNA polymerase I. Alternatively, mung-bean nuclease may be used to cleave the two strands. Mung-bean nuclease and nuclease S1 are similar to one another in their physical and catalytic properties.

5.1.4 Insertion of the RVFV Sequence into a Cloning Vector

After preparation of a dsDNA that is complementary to RVFV RNA, the dsDNA should be prepared for insertion into a suitable vector. This can be accomplished by using the enzyme terminal deoxynucleotidyl transferase (TdT) to attach single-stranded homopolymeric tails to the ends of the dsDNA. This enzyme catalyzes the polymerization of deoxynucleoside triphosphates at the 3'-termini of single-stranded DNA or oligodeoxynucleotides. By using cobalt ion instead of magnesium ion as cofactor, the specificity of the enzyme is changed so that it can be used for terminal labeling and addition of homopolymer tails to duplex DNA fragments. Such incorporation can be made at the 3' hydroxyl-terminus of duplex DNA with either base paired or staggered ends. The homopolymeric tail may be composed of any one of the four nucleotides as the repeating unit: dCTP, dGTP, dATP or dTTP.

The tailed RVFV cDNA is then inserted into a cloning vector that has been cleaved at a unique restriction site and tailed with a homopolymer that is complementary to the 3' tails of the dsDNA molecule. Alternatively, the ends of the dsDNA may be modified by the ligation of DNA linker sequences which encode restriction endonuclease recognition sites. After cleavage at these sites, the dsDNA may be inserted and ligated into a cleaved cloning vector that has complementary ends.

5.1.5. Selection of Transformants Carrying RVFV cDNA Sequences

The resultant recombinant plasmids are then used to transform cells by techniques well known in the art. Transformed cells are selected based upon the expression of gene markers such as antibiotic resistance present on the plasmid. Expression of such markers indicates that the plasmid is replicating. In the example of the present invention, RVFV dsDNA was inserted into pBR322 at the PstI site. Since PstI cleaves pBR322 within its ampicillin resistance gene, cells transformed with a pBR322 recombinant plasmid bearing the RVFV cDNA insert in the PstI site will be ampicillin-sensitive and tetracycline-resistant (the tetracycline resistance gene also borne on the plasmid is unaffected by the cDNA insertion). Cells subjected to the transformation process are therefore grown in the presence of tetracycline such that only cells transformed with functioning plasmids will form colonies (as opposed to nontransformed cells). Upon addition of ampicillin to replicate plates, ampicillin sensitive colonies (i.e., those cells bearing the cDNA insert within the ampicillin resistance gene) stop growing. These ampicillin-sensitive colonies are then picked from the original plates and grown up in culture. Thus, cells transformed with a plasmid bearing the cDNA insert within the ampicillin resistance gene are selected. The determination of whether the cDNA that is inserted into the plasmid is homologous to RVFV RNA sequences may be performed by hybridization techniques using a cDNA probe that is complementary to the M segment of the RVFV RNA.

5.2. Insertion of the RVFV Gene into an Expression Vector

Once RVFV cDNA-containing recombinant plasmids are indentified, the RVFV sequences (hereinafter referred to as an RVFV gene) are subcloned into appropriate expression vectors, i.e., vectors which contain the necessary elements for transcription and translation of the inserted gene (Gautier and Bonewald, 1980, Molec. Gen. Genet. 178: 375). To obtain efficient expression of the RVFV gene (or a portion of the gene), a promoter located 5 to the inserted RVFV gene must be present in the expression vector. RNA polymerase normally binds to the promoter and initiates transcription of a gene or a group of linked genes and regulatory elements. This group is called an operon. Promoters vary in their "strength", i.e., their ability to promote transcription and thus produce large quantities of gene product. Depending upon the host cell system utilized, any one of a number of suitable promoters may be used. For instance, when cloning in an E. coli, its bacteriophages or plasmids promoters such as the lac promoter, trp promoter, recA promoter, ribosomal RNA promoter, the $P_R$ and $P_L$ promoters of coliphage lambda and others may be used to direct high levels of transcription of adjacent DNA segments. Additionally, a hybrid trp-lacUV5 (tac) promoter or E. coli promoters produced by recombinant DNA or other synthetic DNA techniques may be used to provide for transcription of the inserted gene.

When cloning in a eucaryotic host cell enhancer sequences (e.g., the 72 b.p. tandem repeat of SV40 DNA, retroviral long terminal repeats or LTRs, etc.) may be inserted to increase transcriptional efficiency. Enhancer sequences are a set of eucaryotic promoter elements that appear to increase transcriptional efficiency in a manner relatively independent of their position and orientation with respect to a nearby gene. Unlike the classic promoter elements (e.g., the polymerase binding site and the Goldberg-Hogness "TATA" box) which must be located immediately 5' to the gene, enhancer sequences have a remarkable ability to function upstream from, within, or downstream from eucaryotic genes; therefore, the position of the enhancer sequence with respect to the inserted RVFV gene is less critical.

Specific initiation signals are also required for efficient translation in procaryotic and eucaryotic cells. Protein translation is initiated as the result of interaction between two mRNA sites: the ribosome binding site (SD sequence on the DNA complement) and the initiation codon AUG (ATG on DNA). These translation initiation signals may vary in "strength" as measured by the quantity of gene specific protein synthesized. The DNA expression vector, in addition to containing a promoter for transcription, may also contain any combination of various "strong" translation initiation signals.

Thus, any SD-ATG combination that can be utilized by host cell ribosomes may be employed; such combinations include, but are not limited to, the SD-ATG combination from the cro gene or the N gene of coliphage lambda, or from the *E. coli* tryptophan E, D, C, B, or A genes. Additionally, any SD-ATG combination produced by recombinant DNA or other synthetic technique may be used.

Any of the methods previously described for the insertion of DNA fragments into a vector may be used to ligate a promoter and other control elements into specific sites within the vector.

Accordingly, the RVFV gene (or any portion thereof) can be ligated into an expression vector at a specific site in relation to the vector promoter and control elements so that the RVFV gene sequence is in the correct translational reading frame (i.e., in phase) with respect to the vector ATG sequence. The resultant recombinant DNA molecule is then introduced into appropriate host cells by transformation, transduction or transfection (depending on the vector/host cell system). Transformants are selected based upon the expression of appropriate gene markers normally present in the vectors, such as ampicillin resistance or tetracycline resistance in pBR322, or thymidine kinase activity in eucaryotic host systems. Expression of such marker proteins indicates that the recombinant DNA molecule is intact and is replicating. Expression vectors may be derived from cloning vectors, which usually contain a marker function; such cloning vectors may include, but are not limited to the following: SV40 and adenovirus vectors, yeast vectors, bacteriophage vectors such as lambda gt-WES-lambda B, Charon 28, Charon 4A, lambda gt-1-lambda BC, lambda gt-1-lambda B, M13mp7, M13mp8, M13mp9, or plasmid DNA vectors such as pBR322, pAC105, pVA51, pACYC177, pKH47, pACYC184, pUB110, pMB9, pBR325, Col E1, pSC101, pBR313, pML21, RSF2124, pCR1 or RP4.

Cloning in a eucaryotic host system may result in the production of a polypeptide that serves as a better immunogen than those produced by procaryotic transformants due to secondary protein modifications which occur during eucaryotic biosynthesis. Such secondary protein modifications include but are not limited to acylation, glycosylation, methylation, phosphorylation, sulfation and the like. The eucaryotic host cell might modify (i.e., phosphorylate or glycosylate) the clonally derived polypeptide product at sites similar to those of the natural protein.

In addition, host cell strains may be chosen which inhibit the action of the promoter unless specifically induced. In this way, greater than 95% of the vector's promoter's effectiveness may be inhibited in uninduced cells. In certain operons the addition of specific inducers is necessary for efficient transcription and translation of the inserted DNA; for example, the lac operon is induced by the addition of lactose or IPTG (i.e., isopropylthio-β-D-galactoside). A variety of other operons, such as trp, pro, etc., are under different controls. The trp operon is induced when tryptophan is absent in the growth media; and the $P_L$ promoter of lambda is induced by an increase in temperature in host cells containing a temperature sensitive lambda repressor protein, e.g., cI857. Thus, expression of the genetically engineered RVFV protein may be controlled. This is important if production of the protein product of the cloned gene is lethal or otherwise detrimental to the host cells. In such cases, the foreign gene may be replicated but not expressed during growth of the transformants. After the cells reach a suitable density in the growth medium, the promoter can be induced for production of the protein.

One such promoter/operator system is the so-called "tac" or trp-lac promoter/operator system (referred to as "tac") (Russel and Bennett, 1982, Gene 20: 231–243; DeBoer, European Patent Application No. 67,540 filed May 18, 1982, which is herein incorporated by reference). This hybrid promoter is constructed by combining the −35 b.p. (−35 region) of the trp promoter and the −10 p.b. (−10 region of Pribnow box) of the lac promoter (the sequences of DNA which are the RNA polymerase binding site). In addition to maintaining the strong promoter characteristics of the tryptophan promoter, tac is also controlled by the lac repressor (from lac I$^q$). This construction may explain the higher efficiency of expression of this hybrid promoter with respect to either one of the parental promoters.

Gene expression can also be controlled at the level of translation. In non-suppressor cells transformed with amber, ochre, or opal modified plasmids (See Section 5.5.3.), translation of the mRNA produced from the plasmid DNA stops at the nonsense codon and only the desired protein (unfused) is expressed. In an appropriate host (one that is able to "suppress" the nonsense codon), some of the ribosomes, "read through" the nonsense codon and produce fusion protein. Since the level of suppression varies in different host cells, it is possible to regulate the ratio of protein to fusion protein by choosing the appropriate suppressor host cell.

The expression of genes may be regulated in several other ways. For example, in order to improve the initiation of translation, an A/T rich DNA segment may be inserted between the SD$^{cro}$ and the ATG initial codon for the start of translation. An oligomer which contain an A/T rich sequence may be synthesized using state-of-the-art nucleic acid chemistry. A particularly useful method is described in U.S. patent application Ser. No. 491,099 by Kempe, et al., filed May 5, 1983 which is incorporated herein by reference. This A/T rich segment may be needed to destabilize the secondary structure of the mRNA within this region and thereby facilitate ribosome binding and subsequent translation along the message.

In many recombinant clones studied only one translational stop codon (e.g., TAG, TAA or TGA) is present for termination of translation, and no transcriptional-stop like sequences are found in the 3′ untranslated region of the clones. Therefore a triple translational stop sequence, with all 3 nonsense codons may be inserted in phase with the reading frame of the protein. Again, this linker is synthesized using methods referred to above. This construction should then provide for efficient termination of translation by assuring proper translational termination with little chance of readthrough into the 3′ non-coding region of the mRNA.

Recent studies have shown that the tryptophan attenuator region of the tryptophan operon provides for the efficient termination of mRNA transcription from the DNA. This extremely stable stem and loop structure is characteristically GC-rich and posseses dyad symmetry, followed by an oligo-(T) stretch at the site of termination similar to the well known features of rho-independent transcription termination sites in procaryotes. By taking advantage of this system, a sequence comprising the attenuator portion of the tryptophan operon may be placed 3′ of the translational stop codons of the genome. This construction may now allow for the effective termination of transcription of the mRNA.

The regulation of expression of any gene includes, but is not limited to the construction and use of promoter-/operator systems, A/T rich sequences, transcriptional and translational termination sequences, and any other modified gene construct (either naturally occurring or synthetically made) which contributes to an "optimal" system for expression of a protein in a compatible host cell.

5.3 Preparation of Fusion Proteins

To maximize the level of gene expression in a specific transformant it may be desirable to ligate the gene in question to a gene encoding another protein, such as a host cell protein. An additional advantage is obtained if the host cell protein inherently contains an assayable function. The expression of the ligated genes results in a fusion protein product (hereinafter referred to as RVFV fusion proteins) that can be identified on the basis of its large molecular weight and assayable function. For example, production of RVFV/β-galactosidase fusion protein offers several advantages for cloning and expression of RVFV genes in an *E. coli* host. First, this allows for an approximation of the level of protein production (hence expression) directed by the vector using a colorimetric assay specific for β-galactosidase activity according to the method of Miller (pages 47–55 and 352–355 in Experiments in Molecular Genetics, Cold Spring Harbor Press, New York, NY 1972). Second, fusion protein production simplifies the identification and isolation of the protein product. The unfused RVFV protein produced by *E. coli* transformants is smaller than the RVFV/β-galactosidase fusion protein and as such may co-migrate with several other host proteins analyzed by SDS-polyacrylamide gel electrophoresis (SDS-PAGE). However, the fusion protein produced can be easily detected and identified by SDS-PAGE due to its unique large molecular weight. Additionally, hybrid gene sequences, i.e., procaryotic nucleotide sequences ligated to eucaryotic nucleotide sequences, when expressed in procaryotes result in the production of fusion proteins which may be protected from host cell proteolysis, as discussed in Section 2.1.

The present invention is not limited to the production of a β-galactosidase fusion protein; any gene of either eucaryotic or procaryotic origin may be ligated in phase (i.e., in the same translational reading frame) with the RVFV gene to provide advantages similar to the β-galactosidase fusion protein product. Examples include, but are not limited to galactokinase, trp D, E or leader sequences; pilus genes; and eucaryotic genes, such as thymidine kinase, β-globin, SV-40 T-antigen, or Rous Sarcoma Virus transforming gene.

In order to construct a gene which encodes a fusion protein, the two genes must be joined within their coding sequence such that the translational reading frame is maintained and uninterrupted by termination signals. Also, as previously explained, if the host cell is a strain which inhibits the action of the promoter, the fusion protein will be produced only in response to induction.

5.4. Preparation of Unfused Protein

As previously explained, transformants which produce unfused proteins (i.e., unfused to β-galactosidase), generally do so in smaller quantities than transformants which produce fusion proteins; this is true even when the gene sequence for the unfused protein is under the control of an inducible promoter. In addition, the unfused proteins produced by bacterial transformants may be less stable than fusion proteins. In an alternate embodiment of the present invention, a host cell transformant can be engineered to produce, for example, large quantities of both fused RVFV/β-galactosidase fusion protein and unfused RVFV related proteins which will coaggregate and can be purified easily. (See U.S. patent application Ser. No. 573,642 filed Jan. 25, 1984 by George et al., which is herein incorporated by reference.) Three embodiments of this mode of the invention are described in the subsections below.

5.4.1. Co-Transformation of Host Cells

Any appropriate host cell can be co-transformed with two or more plasmids. One plasmid carries the desired unfused protein gene and one plasmid carries a fusion protein gene. Each gene should be under the control of a promoter and translational control elements. The same or different promoter systems may be used to control expression of each gene. If a different promoter is used for each gene sequence then the ratio of the synthesis of the sequences may be controlled by varying the degree of induction of each promoter.

In addition, the two plasmids may carry different selectable drug markers for antibiotic resistance (e.g., tetracycline and ampicillin resistance) and may be maintained within the same cell if grown in the presence of the two antibiotics. With both plasmids in the cell, synthesis of the fusion protein and the labile unfused protein can occur.

These transformed cells produce insoluble aggregates which contain both the unfused proteins and the large fusion protein. There is no requirement that the fusion protein be a RVFV fusion protein. In fact, any combination of fusion protein with unfused protein will have the aggregation and stabilization properties.

For example, a significant stabilization of the unfused Bovine Growth Hormone (hereinafter referred to as BGH) protein was observed when two plasmids were used to transform one host cell, each plasmid directing the synthesis of its respective protein: unfused BGH and porcine parvovirus (PPV)/β-galactosidase fusion protein (PPV/β-galactosidase). Pulse-chase experiments indicated that the half-life of the unfused modified-BGH proteins had increased from a 1–2 minute level to between 30 minutes and 1 hour. Additionally, when these proteins were produced in large amounts within the cell, they formed insoluble aggregates which contain both the unfused BGH protein and the large PPV/β-galactosidase fusion protein. Subsequent purification of the aggregate proteins indicated that the protein could be readily obtained in gram quantities. The cloning and expression of nucleotide sequences encoding BGH is described in detail in U.S. patent application Ser. No. 548,917 by George et al., filed Nov. 7, 1983 which is incorporated by reference herein. The cloning and expression of nucleotide sequences encoding PPV is described in detail in U.S. patent application Ser. No. 564,567 by Halling et al., filed Dec. 22, 1983 which is incorporated by reference herein.

5.4.2. Transformation of Host Cells With One Plasmid Carrying Two Genes

In an alternate embodiment of the present invention, plasmids which carry both the unfused protein gene and the larger fusion protein gene on a single vector are designed and constructed. As described supra for the co-infection scheme, this embodiment of the invention is suitable for any combination of fusion protein and any unfused protein.

The plasmids are constructed such that each gene on the plasmid has its own promoter and expression control elements. The same or different promoter systems may be used to control expression of each gene, therefore this embodiment of the present invention also allows for the regulation of the ratio of the fusion protein and the desired gene product.

5.4.3. Modification of the Fusion Protein Gene

In one embodiment of the present invention, a recombinant plasmid which encodes a RVFV fusion protein is altered at the junction of the two gene sequences which comprise the fusion protein gene. A chain termination sequence such as amber (TAG), ochre (TAA), or opal (TGA) is located between the two gene sequences; the chain terminator must be in phase with the translational reading frames of both gene sequences. Such an alteration may be accomplished by cleaving the plasmid at a restriction site (or sites) located between the two gene sequences and then ligating a nucleotide linker sequence encoding a chain terminator such as amber, ochre, or opal into the cleaved site on the plasmid so that the chain terminator is in phase with the translational reading frames or both gene sequences. (See for example U.S. patent application Ser. No. 510,551, by Watson et al., filed July 6, 1983 which is herein incorporated by reference.)

Introduction of these amber, ochre, or opal modified plasmids into a host cell containing the appropriate tRNA suppressors results in the synthesis of both an unfused protein as well as a fusion protein (since suppression is significantly less than 100%). A tRNA suppressor is a tRNA that has undergone a modification (generally the result of a mutation of the tRNA gene) that allows the tRNA to recognize the termination codon and results in the occasional but not regular insertion of an amino acid at the site of the termination codon. Therefore, host cells carrying the suppressor tRNA characteristically produce both the unfused protein and a fusion protein of normal length. Every nonsense or termination suppressor has a characteristic efficiency, indicated by the fraction of protein chains that are completed.

There are at least two ways to introduce the amber, ochre or opal modified plasmids into a suppressor cell background: (1) the transformant (i.e., a host cell transformed with amber, ochre or opal modified plasmid) can be infected with a lysogenic transducing phage that carries the appropriate suppressor tRNA gene (e.g., φ80 pSU3 carries the supF suppressor of amber mutations); or (2) the amber, ochre or opal modified plasmids can be used to transform cell lines which contain suppressor tRNAs of amber, ochre, or opal respectively. Examples of such strains include but are not limited to LE392 (containing supE and supF suppressors of amber mutations), YMC (containing supF), and C600 (supE). The various amber suppressor tRNA genes in *E. coli* include but are not limited to: supB, supC, supD, supE, supF, supG, supL, supM, supN, supO, supP, supU, supV; the various ochre suppressor tRNA genes in *E. coli* include but are not limited to: supB, supC, supG, supL, supM, supN, supO, supV; and the various opal suppressor tRNA genes in *E. coli* include but are not limited to: supK (see Bachmann and Low, 1980, Microbiological Reviews 44(1): 1–56).

The host cells containing the appropriate suppressor tRNA gene are transformed with the amber, ochre, or opal modified plasmids and can produce the protein as both a fusion protein and as an unfused protein (the proportions of fused to unfused protein produced depends upon the extent of suppression in the host cell).

The amber, ochre, or opal modified plasmids may be further modified to ensure that translation of the corresponding mRNA transcript will terminate at the 3'-terminus of the fusion protein gene. Proper chain termination is important because it contributes to the overall efficiency of translation. A number of approaches which may be used to effect chain termination are described below. In one embodiment, all three chain termination sequences may be inserted in tandem at the 3'-region of the fusion protein gene so that they are in phase with the translational reading frame of the gene sequence. The presence of the chain terminator sequences in tandem will reduce the chance of read-through, consequently, translation will terminate at the chain termination codons on the mRNA transcript.

Alternatively, one or more chain termination sequences of the appropriate type may be inserted into the 3'-region of the fusion protein gene. For example, an amber modified plasmid may be further modified by the insertion (in phase) of one or more opal or ochre sequences at the 3'-end of the fusion protein gene. When this plasmid is inserted into a host cell containing an amber tRNA suppressor (such as supD, supE, supF, supP, supU, supV in *E. coli*) that does not suppress ochre or opal, the host cell will produce both the fusion protein and the unfused protein and translation of the fusion protein will terminate at the location of the opal and/or ochre codons located at the 3'-end of the mRNA transcript.

In a similar fashion, an opal modified plasmid may be further modified by the insertion (in phase) of one or more amber or ochre sequences at the 3'-end of the fusion protein gene. When this plasmid is inserted into a host cell containing an opal tRNA suppressor (such as supK in *E. coli*) that does not suppress amber or ochre, the host cell will produce both the fusion protein and the unfused protein and translation of the fusion protein will terminate at the location of the amber and/or ochre codons located at the 3'-end of the mRNA transcript.

Similarly, an ochre modified plasmid may be further modified by the insertion (in phase) of one or more opal sequences at the 3'-end of the fusion protein gene. When this plasmid is inserted into a host cell containing an ochre tRNA suppressor (such as supb, supC, supG, supL, supM, supN, supO, supV in *E. coli*) that does not suppress opal, the host cell will produce both the fusion protein and the unfused protein and translation of the fusion protein will terminate at the location of the opal codon (or codons) located at the 3'-end of the mRNA transcript.

5.5. Characterization of the Gene Product

Once transformants which contain the correct DNA construction are identified, an analysis of the immunogenicity and antigenicity of the recombinant DNA RVFV gene product is required. Unless the host cell is capable of glycosylating the RVFV gene product in the same pattern as naturally occurring RVFV glycoproteins, the gene product will differ from the natural RVFV glycoprotein. Thus, immunological analysis is especially important for the RVFV gene product since the ultimate goal is to use the recombinant RVFV protein so produced in a vaccine formulation. The analysis of antigenicity is most easily carried out using antisera directed against the authentic RVFV glycoproteins of RVFV-infected cells, whereas immunogenicity is evaluated by analyzing test animal antisera generated by immunization with the recombinant RVFV gene product. The ability of the antisera to neutralize RVFV infection is tested as well as the ability of the recombinant RVFV protein to elicit an immune response capable of protecting animals from an RVFV challenge.

Identification of the proteins described in this invention is, therefore, based upon two requirements. First, the RVFV-related protein should be produced only in response to the induction of the promoter. Second, the RVFV-related protein should be immunologically related to the authentic RVFV proteins; the protein should be immunoreactive whether it results from the expression of the entire gene sequence, a portion of the gene sequence, or from two or more gene sequences which are ligated to direct the production of a fusion protein. This reactivity may be demonstrated by standard immunological techniques, such as immunoprecipitations, immunodiffusion, radio-immune competition, immunoelectrophoresis or the immunological detection of proteins which are separated by polyacrylamide gel electrophoresis and then transferred to nitrocellulose, etc.

5.6. Purification of the Gene Product

Veterinary vaccines may be prepared using host cell lysates or host cell extracts, although certain vaccines might require the use of purified proteins. Furthermore, the purified proteins may be used in diagnostic procedures. In order to purify the proteins produced, cells containing the RVFV gene (or a fragment thereof) are grown up in a large volume and the protein produced after induction of the promoter is isolated from such cells or from the medium if the protein is excreted. The protein may be isolated and purified either by standard chromatography, including ion exchange, affinity or sizing resins, by centrifugation, or by any other standard technique for the purification or proteins.

Since certain fusion proteins form aggregates when overproduced in cells and when in solution, a method for isolating aggregate-forming proteins is particularly useful for isolating the fusion proteins produced in the present invention. These fusion proteins can then be used in vaccine formulation. Purification of fusion proteins (hereinafter referred to as aggregate purification) involves the extraction, separation and/or purification of aggregate-forming proteins by disruption of cells followed by washing the aggregated material. Additionally, the aggregated material may be solubilized by the addition of a solvent that is both a strong hydrogen acceptor and a strong hydrogen donor (or a combination of solvents each having one of these properties); the aggregate-forming proteins may then be precipitated by dilution with a compatible buffer. Suitable protein solvents include, but are not limited to urea (from about 4M to about 8M), formamide (at least about 80%, volume/volume basis), and guanidine hydrochloride (from about 4M to about 8M). Some solvents which are capable of solubilizing aggregate-forming proteins, for example SDS (sodium dodecyl sulfate), 70% formic acid, are inappropriate for use in this procedure because subsequent precipitation of the solubilized aggregate-forming proteins has proved to be inefficient. Although guanidine hydrochloride and other similar agents are denaturants, studies indicate that this denaturation is not irreversible and that renaturation may occur upon removal (by dialysis, for example) or dilution of the denaturant, allowing re-formation of immunologically and-/or biologically active protein.

One embodiment of the fusion protein isolation technique is outlined as follows (hereinafter referred to as the non-denaturing aggregate purification procedure): the cell pellet is quick frozen using dry ice/methanol, weighed, and 3–4 g of cells are resuspended in at least 25 ml of a buffer solution [e.g., 50 mM Tris-HCl (tris hydroxymethylaminomethane-hydrochloride), pH 8.0, 2 mM EDTA (ethylenediaminetetraacetic acid) and 200 mM NaCl]. That is, the cells are suspended in a buffer solution at an approximate concentration of from about 100 to 200 grams of cells/liter. Concentrations less than about 160 grams/liter are preferred. To this suspension lysozyme is added to a final concentration of about 130 ug/ml and the resulting mixture is allowed to stand at 4° C. for 20 minutes with occasional shaking. Nonidet P40 (NP-40, Shell trademark, polyoxyethylene (9) p-tert-octylphenol), a non-ionic detergent used to solubilize membranes, is added to a final concentration of about 0.1–1% and the solution mixed. Then, the suspension is ground for approximately 1 minute using a Polytron grinder (Brinkman Instruments, Westbury, NY) or equivalent.

The suspension is centrifuged at $8,000 \times g$ for 30 minutes, and the pellet resuspended in a wash buffer, e.g., 20 mM Tris-HCl (pH 7.2), 1 mM EDTA, 150 mM NaCl and 2% Triton-X 100 (polyoxyethylene (9–10) p-tert-octylphenol, a non-ionic detergent), and ground with the Polytron grinder. This step of centrifugation, washing, and grinding may be repeated to further wash the pellet and remove as much cellular debris as possible.

Alternatively, the pellet of aggregates may be further treated by the addition of a denaturant (hereinafter referred to as the denaturing aggregate purification procedure) as follows: The suspension is centrifuged, the supernatant removed completely and the pellet resuspended in about one-fifth volume of 6M guanidine hydrochloride (in distilled water). For instance, 3 g of cells washed with 25 ml of buffer should be resuspended at this step in 5 ml of 6M quanidine hydrochloride solution. It may be difficult to resuspend the pellet at this stage and sonication or homogenization may be required in order to obtain a homogenous solution. The solution is allowed to stand at 22° C. for 20 minutes and is then centrifuged at $8,000 \times g$ for 30 minutes to remove debris, saving the supernatant which at this point contains the fusion protein.

The fusion protein is precipitated from the guanidine hydrochloride supernatant by the addition of about four volumes of aqueous buffer. Almost any aqueous buffer may be used at this stage; however, the addition of a small amount of non-ionic detergent, such as 0.5% NP-40 or Triton X-100 may be helpful. This suspension is allowed to stand at 4° C. for 30 minutes and is then centrifuged at $8,000 \times g$ for 10 minutes. The supernatant is discarded, the pellet (containing the fusion protein precipitate) is resuspended in an appropriate buffer, e.g., Phosphate Buffered Saline (PBS) in any appropriate volume. Brief sonication or homogenization may aid in obtaining a homogenous suspension or slurry.

It may be desirable to remove any remaining DNA from the suspension of aggregates or the fusion protein precipitate before using either as an immunogen. To this end the suspension of aggregates or fusion protein precipitate is pelleted and resuspended in wash buffer containing no detergent. To either suspension a final concentration of about 10 mM MgCl$_2$ and 2 ug/ml Deoxyribonuclease I (P.L. Biochemicals, Milwaukee, WI) is added. After incubation at 37° C. for 30 minutes, the suspension of aggregates or fusion protein precipitate is pelleted by centrifugation, washed with buffer, repelleted, and resuspended in fresh buffer, thus removing most of the deoxyribonuclease.

According to the denaturing aggregate purification procedure, fusion proteins may also be solubilized in 8M urea and subsequently dialysed to remove the urea. This is carried out by adding solid urea to a final urea concentration of 8M. Also added are EDTA to 10 mM, DTT to 1 mM and Tris, pH 7.5 to 50 mM. The urea is then removed by dialysis usually against PBS.

Another embodiment of the fusion protein isolation technique involves purification of aggregate proteins from larger volumes of culture. This method is a modification of the aggregate purification procedure described supra. The cell pellet is quick frozen in a dry ice/ethanol bath, weighed, and approximately 30–60 g of cells are resuspended in 125 ml of BIP buffer (50 mM Tris pH 8.0, 10 mM EDTA) at 37° C. with shaking for 10 minutes. The partially resuspended cells are homogenized using a Polytron grinder (Brinkman Instruments, Westbury, NY). To this suspension 50 mg of lysozyme (10 mg/ml in BIP) is added while the cells are further homogenized and the cells are placed at room temperature for 20–30 minutes. Nonidet P40 (described supra) is added to a final concentration of 0.1% and the mixture is homogenized using a Polytron grinder for 5 minutes.

The cell lysate is centrifuged at 26,890×g for 20 minutes using a SS-34 Sorvall rotor and the supernatant is discarded. The pellet is resuspended in 150 ml B2P buffer (10 mM Tris pH 7.5, 1 mM EDTA, 1% Triton X-100), homogenized for 2–5 minutes, and centrifuged for 20 minutes at 26,890×g. This step is repeated, and the pellet (containing the aggregate protein) is then washed two times with water. Finally, the aggregate protein is resuspended in water using the Polytron grinder.

In an alternate embodiment of the present invention, aggregates purified as described supra containing fused and unfused protein are solubilized, and soluble unfused viral protein is isolated. Aggregate protein (4 mg/ml) is suspended in 20 ml of buffer (75 mM Tris-HCl, 10M urea, and 0.5M β-mercaptoethanol), sonicated for 2 minutes, and heated at 65° C. for 30 minutes. The suspension is centrifuged at 20,000×g for 20 minutes, and the supernatant is diluted by the addition of an equal volume of water.

The sample is applied to a 30 ml DE52 (Diethylaminoethyl cellulose, Whatman Chemical Separation Ltd., Kent, England) column. The column is washed with several volumes of buffer (30 mM Tris-HCl, 4M urea, 50 mM β-mercaptoethanol, pH 9.0). The protein is eluted from the column using a gradient from 0 to 150 mM NaCl (400 ml of buffer containing 30 mM Tris-HCl, 4M urea, 50 mM β-mercaptoethanol, pH 9.0).

Fractions are collected and an aliquot of each fraction is analyzed by SDS-PAGE for the presence of unfused protein, Fractions containing unfused protein are pooled and dialyzed against 30 mM Tris-HCl, pH 9.0. Finally, the unfused protein is neutralized and concentrated at least 10 fold by ultrafiltration using an Amicon Model #8050 Ultrafiltration Cell (Amicon Corp., Danvers, MA).

Alternatives to purification of the protein from genetically engineered recombinants include synthesis of polypeptides of RVFV which are immunogenic and antigenic. Once the RVFV glycoprotein genes are identified by the techniques described herein, their amino acid sequences can be deduced. Then, any method such as solid phase protein synthesis and the like can be used to synthesize these polypeptides or relevant portions thereof. These polypeptides may be used in vaccine formulations or in diagnostic assays.

5.7. Formulation of a Vaccine

The purpose of this invention is to produce, by recombinant DNA techniques, an RVFV glycoprotein-related polypeptide which may be used as an immunogen in a vaccine to protect against RVFV infections in humans or animals. If the protein produced is immunoreactive with specific RVFV neutralizing antibodies, it would be expected to elicit an immune response capable of neutralizing the virus. Vaccines made from genetically engineered immunogens should be safer than conventional vaccines made from attenuated virus because there is no risk of infection of the recipient.

Alternatively, the genetically engineered RVFV product may be used to produce antibodies for use in passive immunotherapy or as a diagnostic tool. For instance the RVFV specific antibody may be labeled with a dye, an enzyme such as peroxidase, ferritin, a fluorescent compound, or a radioactive compound. Such a labeled antibody may be used to detect RVFV antigens (and, therefore, RVFV) in various body fluids obtained from animals suspected to be infected with RVFV. Such techniques for immunoassay in vitro diagnostic assays are well known and may be applied to body fluids obtained from mucous membranes, semen, blood and excrement. Finally, the genetically engineered product may be used as antigen in an in vitro immunoassay to determine and monitor the titers of antisera in vaccinated animals.

Although the RVFV/β-galactosidase fusion protein product itself may be useful in a vaccine formulation, it may be advantageous to first remove and/or modify all or part of the β-galactosidase moiety in order to produce a more effective RVFV-related immunogen.

While whole cells or crude extracts of induced transformants may be used to vaccinate animals, the genetically engineered RVFV protein may isolated and purified from the host cells using standard protein isolation techniques or the purification scheme described in Section 5.7. The final purified product may then be diluted to an appropriate concentration and formulated with any suitable vaccine adjuvant and packaged for use. Suitable adjuvants include but are not limited to: Freund's adjuvant (complete or incomplete), Adjuvant 65 (containing peanut oil, mannide monooleate and aluminum monostearate), and mineral gels such as aluminum hydroxide, aluminum phosphate, alum, surface active substances, e.g, hexadecylamine, octadecylamine, lysolecithin, dimethyldioctadecylammonium bromide, N,-N-dioctadecyl-N'-N-bis(2-hydroxyethylpropane diamine), methoxyhexadecylglycerol, and pluronic polyols; polyanions, e.g., pyran, dextran sulfate, poly IC, polyacrylic acid, carbopol; peptides, e.g., muramyl dipeptide, dimethylglycine, tuftsin and oil emulsions. Finally, the protein product may be incorporated into liposomes for use in a vaccine formulation, or may be conjugated to polysaccharides or other polymers. (Freund's adjuvant is no longer used in vaccine formulations for humans or for food animals because it contains nonmetabolizable mineral oil and is a potential carcinogen; however, the mineral gels are widely used in commercial veterinary vaccines.)

The genetically engineered DNA molecules described herein allow great flexibility for vaccine production. For example, a vaccine could be formulated using a RVFV-related protein produced by transformants containing any portion of the RVFV-related gene sequence or a recombinant DNA molecule which contains multiple copies of the RVFV gene (or portion(s) thereof) in tandem. The RVFV gene sequence (or portion thereof) may be ligated to genes that encode other immunogens so that the fused protein product could be used in the preparation of multivalent vaccines. Additionally, the glycoprotein gene sequence (or portion thereof) could be ligated to other RVFV glycoprotein gene sequences (or portions thereof) in any combination. Finally, the RVFV sequence may be reorganized to increase the immunogenicity of the vaccine. For example, the gene sequence may be altered so that the protein product presents specific epitopes to the immune system (e.g., an antigenic site of the glycoprotein that is normally unexposed to the immune system); or the regions of the protein gene sequences that encode immunosuppressive portions of the protein can be deleted.

6. EXAMPLE

Figure 1:
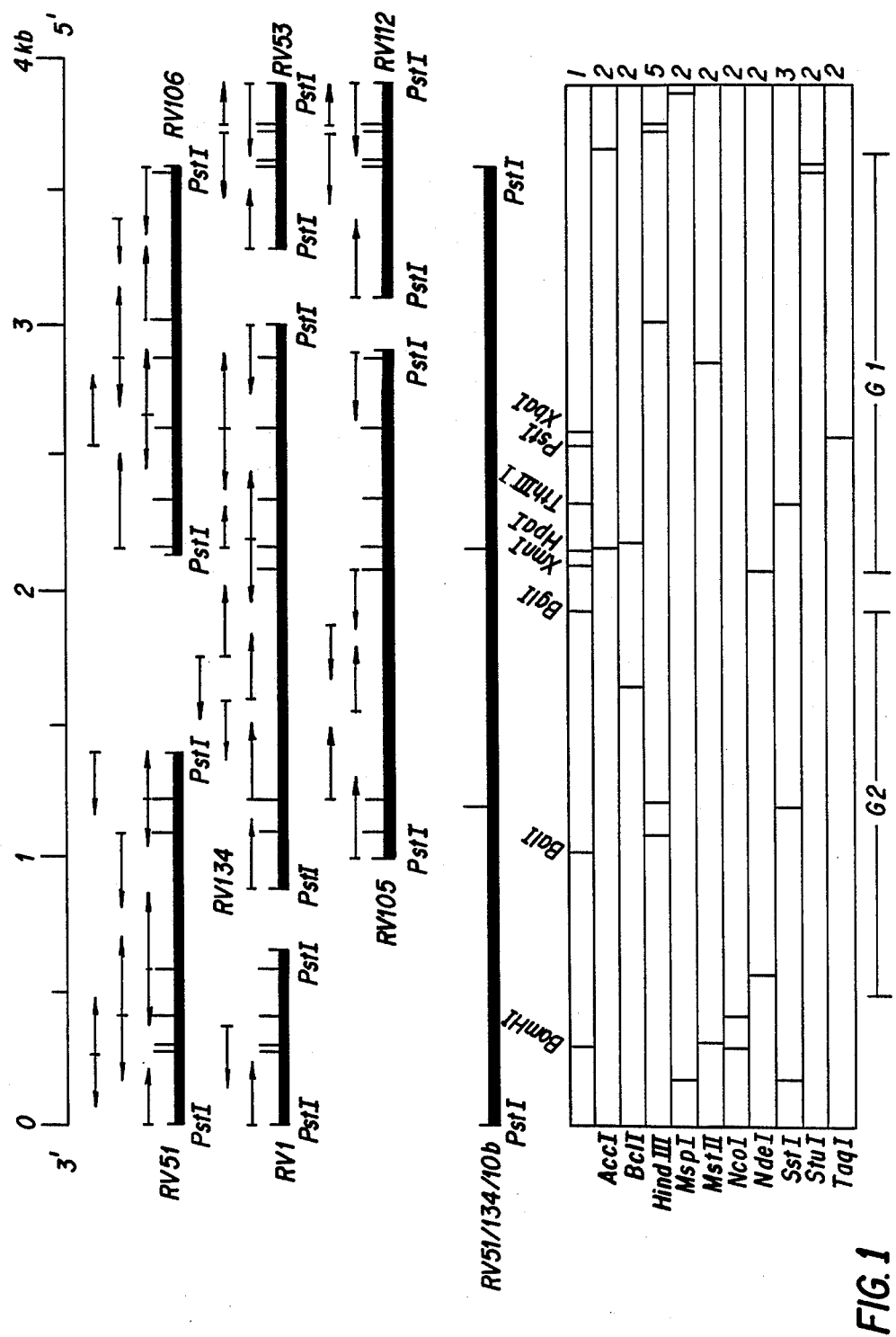

According to one embodiment of the method of the present invention the RVFV genetic sequences were cloned by inserting the cDNA fragments of the RVFV M RNA into the vector pBR322 to form several recombinant plasmids, each of which contained a different portion of the RVFV genome (See FIG. 1). The plasmids containing these RVFV M RNA sequences were identified by hybridization using cDNA specific for the M RNA segment as a probe.

Once plasmids containing the RVFV sequences were identified, the RVFV-related DNA was characterized by restriction enzyme mapping and DNA sequencing. Plasmids pRV1, pRV51 pRV53, pRV105, pRV106, pRV112, pRV134 and pRV51/134/106 contained genetic information derived from the M RNA. Portions of these RVFV-specific DNAs were subcloned into the expression vectors pCJ423, pHK414 and pJS413 to yield recombinants designated pRVE-451, pRVE414-51, pJSRV-134HpX, pCJRV-134P, pRVE-BHpa-20, pHKRV-106, and pHKRV-106st. Portions of these RVFV-specific DNAs were also subcloned into the expression vectors ptc412, ptc413, and ptc414 to yield recombinants designated ptRV-BHF, ptRV-BH, ptRV-106SF, ptRV-106S, ptRV-C12 and ptRV-C12T. These recombinants allow for the production in E. coli of proteins expressed from the inserted RVFV genetic information. The RVFV-related proteins produced by the E. coli transformants are non-glycosylated and thus differ from the naturally occurring RVFV glycoprotein. However, the RVFV-related proteins are immunoreactive with antibodies directed against authentic RVFV and are themselves immunogenic.

6.1. General Procedures Used for Preparation of the Plasmids

The following subsections describe the general procedures and materials used for genomic RNA isolation, enzymatic reactions and ligation reactions.

6.1.1. Plasmid DNA Isolation

Host cell bacteria E. coli were transformed and large (microgram) quantities of plasmid DNA were isolated from cultures of E. coli transformants grown in M-9 broth (Miller, Experiments In Molecular Genetics, Cold Spring Harbor Press, New York, NY, 1972). Plasmids were isolated from cells in late logarithmic stage of growth using a modification of the method of Guerry (Guerry, et al., 1973, J. Bacteriol. 116: 1063).

6.1.2. Conditions For Restriction Enzyme Digestions

Restriction enzymes used in the present application were obtained from New England Biolabs, Inc. (Beverly, MA). An enzyme unit is defined as the amount required to digest 1.0 ug of lambda DNA in 60 minutes at 37° C. in a total reaction mixture of 50 ul as described by the manufacturer.

Unless otherwise indicated all restriction enzyme total digestions were accomplished under the following conditions: each 1 ug of DNA was incubated with 0.5 units of enzyme at 37° C. for 60 minutes in 20 ul buffer. Partial digestions were accomplished by modifying the conditions used for total digestion as follows: each 1 ug DNA was incubated with 0.1 units of enzyme at 37° C. for 15 minutes. Reactions were terminated by the addition of 0.1% SDS. Thus, the reaction conditions were adjusted to obtain an average of one cleavage per DNA molecule. Complete or partial restriction enzyme digestions were monitored by agarose gel electrophoresis of an aliquot of the reaction mixture. Restriction digestion is indicated in each case by the correct size and number of DNA fragments which are detected as discrete bands in the gel.

6.1.3. Restriction Enzyme Buffers

The buffer used for SphI digestions consisted of: 150 mM NaCl, 10 mM Tris-HCl (pH 7.4), 10 mM MgCl$_2$, and 6 mM β-mercaptoethanol (β-ME).

The buffer used for BamHI, BglII, HindIII, PstI, PvuII, RsaI, StuI, SstI and XbaI digestions consisted of: 100 mM NaCl, 10 mM Tris-HCl (pH 7.4), 10 mM MgCl$_2$, and 6 mM β-ME.

The buffer used for HpaI and SmaI digestions consisted of: 20 mM KCl, 10 mM Tris-HCl (pH 7.4), 10 mM MgCl$_2$, and 6 mM β-ME.

It should be noted that whenever two or more restriction endonuclease reactions are performed on DNA, the reaction in low salt buffer is accomplished before the reaction in high salt buffer. If two enzymes require the same buffer, then the reactions may be performed simultaneously.

6.1.4. Modification of DNA

Mung-bean nuclease degrades single-stranded DNA to mono- or oligonucleotides with phosphate groups at their 5' ends. Double-stranded DNA, double-stranded RNA, and DNA-RNA hybrids are relatively resistant to the enzyme. One unit of mung-bean nuclease (P.L. Biochemicals, Milwaukee, WI) is that amount of enzyme which produces one microgram of acid-soluble material per minute at 37° C. The reaction mixture contains 50 mM sodium acetate (pH 4.5), 300 mM NaCl, and 1 mM ZnCl$_2$. One unit of mung-bean nuclease was then added and 0.060 ml aliquots were taken at 5, 10, 20 and 30 minutes of incubation to monitor the extent of digestion. The reaction was terminated by addition of EDTA (10 mM final concentration) followed by phenol extraction.

6.1.5. Gel Purification of DNA Fragments

After restriction enzyme or nuclease treatment, DNA fragments of varying sizes were separated by gel electrophoresis in either agarose or polyacrylamide slab gels at low voltage (approximately 2 volts/cm for agarose gels and 10 volts/cm for polyacrylamide gels), stained with 0.5 ug/ml ethidium bromide and visualized under ultraviolet light (Maniatis et al., 1982, Molecular Cloning, A Laboratory Manual, Cold Spring Harbor, NY).

In order to recover particular DNA fragments from gels, the appropriate bands were sliced out of the gel and the DNA was electroeluted into dialysis tubing. The DNA was then isolated on DEAE-cellulose, or ethanol precipitated, and resuspended in the appropriate buffer (Aviv and Leder, 1972, Proc. Nat. Acad. Sci., U.S.A., 69: 1408).

Another method of recovering DNA from gels was by using low melting point (LMP) agarose. Electrophoresis was carried out as above. After electrophoresis, the DNA was stained with ethidium bromide and the DNA band was then sliced out of the gel. The band slice was placed in a small tube, heated at 65° C. until the agarose completely melted (2-5 minutes), extracted with phenol and ethanol precipitated (Maniatis et al., 1982, Molecular Cloning, A Laboratory Manual, Cold Spring Harbor, NY).

6.1.6. DNA Ligation

All ligations were accomplished using T4 DNA ligase (New England Biolabs, Inc., Beverly, MA). One unit of T4 DNA ligase is defined as the amount required to yield 50% ligation of HindIII fragments of bacteriophage lambda DNA in 30 minutes at 16° C. in 20 ul of ligase buffer and a DNA concentration of approximately 300 ug/ml.

DNA ligations were carried out in ligase buffer consisting of: 20 mM Tris-HCl (pH 7.8), 10 mM MgCl$_2$, 60 mM $\beta$-ME, 1.0 mM ATP and a DNA concentration ranging from 10-30 ug/ml. Ligation reactions were incubated 4 to 24 hours at room temperature using approximately 300 units of T4 DNA ligase per 20 ul reaction volume.

6.2. Isolation and Molecular Cloning of the RVFV Genome

The genome of the RVFV is composed of ribonucleic acid (not deoxyribonucleic acid), therefore, before insertion into a DNA vector, the genomic code was converted from RNA to DNA using the enzyme reverse transcriptase. A single-strand of cDNA was first made and then a second, complementary strand was made. The cDNA was then modified inserted into cloning vectors to create various recombinant plasmids, each containing a defined portion of the RVFV genome. These recombinant plasmids were then used to characterize the RVFV genetic sequences, and subsequently served as sources of RVFV genetic information for expression cloning. Details are described below.

6.2.1. Isolation of RVFV Genomic RNA

The Zagazig Hospital isolate 501 (ZH501) of RVFV was used to infect Vero cells grown in roller bottles. Culture fluids (400 ml) were harvested approximately 20 hours after infection and clarified by centrifugation at 1500$\times$g for 15 minutes. An equal volume of saturated ammonium sulfate solution was slowly added to the cleared culture fluid. This mixture was stirred at 4° C. for 4 hours, centrifuged at 10,000$\times$g for 45 minutes, and the pelleted material was resuspended in a total final volume of 20 ml of STE buffer (150 mM NaCl, 10 mM Tris-HCl, pH 7.2, 1 mM EDTA). After dialysis against STE for 16 hours at 4° C., the material was divided equally and layered onto three linear 15-60% sucrose (in STE) gradients and centrifuged at 4° C. in a SW27 rotor (Beckman Instruments, Fullerton, CA) for 4 hours at 25,000 rpm (82,500$\times$g). One ml fractions were collected, the virus peaks were localized spectrophotometrically (by absorbancy of the fractions at O.D. 260) pooled, and then diluted with five volumes of STE. The virus was then pelleted by centrifugation at 4° C. in a SW27 rotor at 25,000 rpm for 2 hours. The pellet was resuspended in 1 ml of TE-1 (10 mM Tris-HCl, pH 7.2, 1 mM EDTA), adjusted to 2% Triton X-100, and incubated at 22° C. for 40 minutes. This material was then layered onto a linear 18-30% sucrose gradient (in STE) and centrifuged at 4° C. in a SW41 rotor (Beckman Instruments, Fullerton, CA) at 40,000 rpm (197,000$\times$g) for 4 hours. Fractions (0.3 ml) were collected, and the three nucleocapsid peaks (designated L, M, and S) localized by absorbancy at O.D. 260. Fractions containing the M nucleocapsids were pooled, diluted with three volumes of STE, extracted two times with phenol, and ethanol precipitated several times. The resultant M RNA was recovered by centrifugation (16,000$\times$g for 30 minutes) and resuspended in a small volume of water.

6.2.2. Preparation of cDNA from Genomic RVFV RNA

Purified RVFV RNA was prepared for production of complementary DNA by first adding poly(A) to the 3' termini of the RNA using E. coli poly(A) polymerase. One unit of the enzyme incorporates 1 nmol of AMP into tRNA in 10 minutes at 37° C. RVFV M RNA (600 ug) was dissolved in 300 ul buffer (10 mM MgCl$_2$, 10 mM Tris-HCl (pH 7.2) and treated with DNase (20 ug/ml) for 30 minutes at 37° C. The reaction was stopped by the addition of SDS to 1% and extracted with phenol:chloroform:isoamylalcohol (24:24:1) three times. RNA was ethanol precipitated three times and treated with poly(A) polymerase. The reaction buffer used for poly(A) polymerase consisted of: 50 mM Tris-HCL (pH 7.9), 10 mM MgCl$_2$, 2.5 mM MnCl$_2$, 0.25M NaCl. Incubations were in a total volume of 0.3 ml at 37° C. for 10 minutes using 30 units of enzyme. The reaction mixture was extracted with phenol:-chloroform:isoamylalcohol (24:24:1) followed by a chloroform/isoamylalcohol extraction and ethanol precipitation of the nucleic acid.

Polyadenylated RNA was separated from non-polyadenylated RNA by chromatography on oligo(dT)-cellulose (Aviv and Leder, 1972, Proc. Nat. Acad. Sci., U.S.A. 69: 1408). The RNA from the polyadenylation reaction was dissolved in an application buffer consisting of 0.01M Tris-HCl (pH 7.2), 1 mM EDTA and 0.5% SDS and heated for 2 minutes at 70° C. NaCl then was added to the buffer to a final concentration of 0.5M. This RNA solution was then applied to the column. The polyadenylated sequences on the RNA molecules bind via hydrogen bonding to the complementary oligo(dT) sequences chemically attached to the cellulose. Non-adsorbed RNA (presumably non-polyadenylated RNA) is eluted by extensive washing with the application buffer. The polyadenylated RNA is then removed from the column by elution with buffer containing no sodium chloride.

The next phase of the invention involved the reverse transcription of the RVFV polyadenylated RNA to yield a complementary DNA molecule (i.e., cDNA). This process was performed by the enzyme RNA-directed DNA polymerase (reverse transcriptase). This enzyme uses RNA as a template for the synthesis of a complementary strand of DNA. The presence of a primer containing a free 3'-OH group which anneals to the RNA template is necessary for transcription. The enzyme transcribes the RNA in the 3' to 5' direction and adds deoxynucleoside monophosphates sequentially according to the base pattern dictated by the RNA template. Here, where the 3' end of the RNA template contains poly(A), a convenient primer to use is an oligo(dT) molecule. The deoxythymidylate chain anneals to the poly(A) portion of the RNA chain and provides the necessary primer for the reverse transcriptase enzyme. One unit of activity of reverse transcriptase (Life Sciences, St. Petersburg, FL) is the amount of enzyme which incorporates one nmol of deoxythymidine-5'-triphosphate into acid precipitable product in 1 minute at 37° C. using poly(dA)-oligo(dT) as the template-primer. The reverse transcriptase reaction mixture consisted of the following: 50 mM Tris-HCl (pH 8.2), 6 mM MgCl$_2$, 1 mM $\beta$-ME, 40 mM KCl, dCTP, dGTP, dATP and dTTP (P.L. Biochemicals, Milwaukee, WI) all present at 200 uM, 25 ug/ml oligo(dT), 500 units/ml RNasin (Biotech, Madison, WI) 100 ug/ml poly(A)-RVFV RNA, and 200 units/ml reverse transcriptase in a total volume of 0.2 ml. The reaction was allowed to incubate for 1.5 hours at 37° C. and was stopped by the addition of 12 ul of 5N NaOH, 10 ul 0.2M EDTA, pH 7.2, and incubated at 70° C. for 20 minutes. The NaOH also destroys the RNA leaving only the cDNA. The cDNA was neutralized by the addition of 12 ul 5N HCl, phenol-extracted and ethanol precipitated.

Double-stranded cDNA was synthesized from the single-stranded cDNA in the following manner: the 3' ends of most single-stranded cDNA's are capable of forming hairpin structures and therefore can be used to prime the synthesis of the second cDNA strand by *E. coli* DNA polymerase I. In this invention, the Klenow fragment of *E. coli* DNA polymerase I was used as the polymerizing enzyme. In a total volume of 0.04 ml, 1.8 ul Klenow fragment *E. coli* DNA polymerase I (7 units, Bethesda Research Laboratories, Gaithersburg, MD), dATP, dCTP, dTTP, dGTP (300 uM each), 0.01M MgCl$_2$, 0.1M KCl, 0.02M Hepes bufffer (4-(2-Hydroxyethyl)-1-piperazine ethane sulfonic acid), pH 6.9, and [alpha-$^{32}$P]-dATP (180 uCi, New England Nuclear, Boston, MA). The reaction mixture was incubated for 18 hours at 15° C.

Since the primer for the Klenow fragment was the hairpin structure of the 3' end, the resulting double-stranded DNA molecule contained a hairpin loop at one end. This loop was removed by limited digestion with mung-bean nuclease. The reaction mixture (250 ul) contained 0.02M sodium acetate (pH 4.6), 0.05M NaCl, and 1 mM ZnCl$_2$, 5% glycerol, and the double-stranded cDNA. One unit (see Section 6.1.4.) of the mung-bean nuclease was then added and 0.060 ml aliquots were taken at 5, 10, 20 and 30 minutes to monitor the extent of digestion. The reactions were terminated by extraction of the reaction solution with phenol.

6.2.3. Insertion of RVFV cDNA into Cloning Vectors

Homopolymeric tails of deoxycytidylic acid [poly(dC)] were attached to the cDNA employing the enzyme TdT (terminal deoxynucleotidyl transferase, P-L Biochemicals, Inc., Milwaukee, WI) under the following reaction conditions: 14 units of TdT, (one unit of enzyme incorporates 1 nmol d(A) into oligonucleotides per minute at 37° C.), 0.1 mM dCTP (P.L. Biochemicals, Milwaukee, WI), 140 mM potassium cacodylate (pH 7.2), 1 mM CoCl$_2$, 0.1 mM dithiothreitol (DTT) and 12 ug/ml cDNA. After incubation for 5 minutes at 37° C., the reaction was terminated by addition of EDTA (10 mM final concentration) and heating to 65° C. for 5 minutes.

The tailed RVFV cDNA was then inserted into a cloning vector that had been cleaved at a unique restriction site and tailed with a homopolymer that is complementary to the 3' tails of the cDNA molecule. Since the cDNA was poly(dC)-tailed, the circular plasmid pBR322 was cleaved with the restriction enzyme PstI (resulting in cleavage at a unique site on the plasmid) and tailed with deoxyguanidine (poly(dG)-tailed) as described above. After digestion with PstI for 2 hours with 1 unit of enzyme per ug DNA, the reaction was terminated by adjusting the reaction mixture to a final concentration of 10 mM EDTA, 0.5% SDS and incubating at 65° C. for 20 minutes. The mixture was then extracted once with STE-saturated phenol (STE is 150 mM NaCl, 10 mM Tris-HCl (pH 7.2), 1 mM EDTA), adjusted to 300 mM sodium acetate and ethanol precipitated three times with 2.5 volumes cold absolute ethanol.

The final precipitate, which consisted of linear pBR322 with 3'-staggered termini, was resuspended in water for (dG)-tailing. The suspension was adjusted to 140 mM potassium cacodylate (pH 7.2), 1 mM CoCl$_2$, 0.1 mM DTT, and 100 uM dGTP; (dG)-tailing was initiated by the addition of TdT at a concentration of 3 units per ug DNA (P.L. Biochemicals, Inc., Milwaukee, WI) and incubated for 20 minutes at 37° C. The reaction was stopped by the addition of EDTA to 10 uM and heating at 65° C. for 10 minutes. The linear vector with (dG)-tails was annealed with the (dC)-tailed cDNA to form a recircularized recombinant plasmid containing the RVFV cDNA insert by adding the following to the linear, (dG)-tailed pBR322 vector (100 ng): 100 mM NaCl, 0.01M Tris-HCl (pH 7.2), 1 mM EDTA and (dC)-tailed RVFV cDNA (300 ng). The solution was heated to 65° C. for 25 minutes and then cooled to 42° C. and incubated for 2 hours.

The resulting mixture was used to transform an *E. coli* host, strain MC1000 (Cassadaban and Cohen, 1980, J. Mol. Biol 138: 179–207). Primary tranformants were assayed for drug resistance (the ampicillin and tetracycline resistance genes are carried on the vector). If the cDNA has been successfully inserted into the pBR322 plasmid, it interrupts the gene coding for the $\beta$-lactamase and the phenotype will be ampicillin sensitive/tetracycline resistant. The colonies are first screened for tetracycline resistance and then the tetracycline resistant colonies are tested for ampicillin sensitivity. Several hundred bacterial colonies exhibiting the correct phenotype (ampicillin sensitivity, tetracycline resistance) were generated.

6.2.4. Identification of Bacterial Colonies Containing RVFV Sequences Derived from the M RNA To identify specific bacterial colonies containing recombinant plasmids with RVFV gene sequences derived from the M RNA, a radioactive probe representing the M RNA was made and used as a hybridization reagent. Specifically, viral genomic RNA was electrophoresed in a low melting point (LMP) agarose gel, the M RNA species was localized by ethidium bromide staining and illumination with long UV light and the appropriate bands were excised from the gel. The RNA was extracted from the gel slices with phenol (Maniatis et al., 1982, Molecular Cloning, A Laboratory Manual, Cold Spring Harbor, NY). After several ethanol precipitations, the gel-purified M RNA (about 100 ng) was resuspended in 20 ul water and boiled for 2 minutes in the presence of 10 ug of calf thymus oligonucleotide primers (prepared as described by Taylor et al., 1976 Biochem. Biophys. Acta 442: 324). It was then added to a reaction mixture in a final volume of 100 ul composed of: 50 mM Tris-HCl, pH 8.0, 10 mM $MgCl_2$, 40 mM KCl, 30 mM β-ME, 200 uM each of dGTP, dCTP, and dTTP, 200 uCi of [alpha-$^{32}$P]-dATP, and 10 units of reverse transcriptase. After 60 minutes at 37° C., the reaction mixture was boiled for 1 minute, phenol extracted, and ethanol precipitated several times. This resultant [$^{32}$P]-cDNA representative of M RNA sequences was then used as a probe in a standard colony hybridization experiment to detect bacterial clones containing DNA sequences related to the probe (Maniatis et al., 1982, Molecular Cloning, A Laboratory Manual, Cold Spring Harbor, NY). Briefly, bacterial colonies exhibiting the correct drug resistance phenotype were grown on L agar dishes containing 20 ug/ml tetracycline. These colonies were then transferred to Whatman 541 filter paper and sequentially placed (colony side up) on two layers of Whatman 3MM paper saturated with the following solutions for 7 minutes each in order to lyse the cells: (i) 0.5M NaOH; (ii) 1M Tris-HCl, pH 7.4; (iii) 1M Tris-HCl pH 7.4, and (iv) 1.5M NaCl, 0.5M Tris-HCl, pH 7.4. The filters were then dried at 80° C. for 2 hours. Filters were then incubated at 68° C. for 2 hours in hybridization buffer (0.75M NaCl, 0.075M sodium citrate, 2 mM EDTA, 0.1% SDS, 50 ug/ml yeast tRNA, 0.02% bovine serum albumin (Pentax Fraction V, Miles Laboratories, Elkard, IN), 0.02% polyvinylpyrrolidone, 0.02% Ficoll (a non-ionic synthetic polymer of sucrose, Sigma Chemical, St. Louis, MO), after which the [$^{32}$P]cDNA probe was added and the incubation continued at 68° C. for 15 hours. The filters were washed 2 times, 30 minutes each, in 0.3M NaCl, 0.03M sodium citrate, 0.1% SDS at 22° C., followed by two similar washes at 68° C. The filters were then rinsed in $H_2O$, dried, and exposed to X-ray film. Approximately 170 colonies were found to contain plasmids in which RVFV M RNA sequences were represented. Seven plasmids, pRV1, pRV51, pRV53, pRV105, pRV106, pRV112 and pRV134, each of which contains various portions of the RVFV genome, are depicted in FIG. 1.

6.2.5. Restriction Mapping and DNA Sequencing of RVFV cDNA

Many of the recombinant DNA plasmids found to contain M RNA sequences were isolated and screened for the size of their RVFV-specific insert DNA. This was done by restricting the plasmids with the PstI restriction endonuclease, and analyzing the resultant digestion products by agarose gel electrophoresis. The method of cloning the dC-tailed RVFV cDNA into the (dG)-tailed PstI site of plasmid vector pBR322 (described in section 6.2.3.) usually results in the generation of PstI restriction sites at the boundaries of the vector DNA and insert cDNA. Thus cleavage of such recombinant plasmids with the PstI enzyme will serve to release the inserted RVFV DNA from the pBR322 vector backbone. Any PstI enzyme sites present within the insert DNA will result in the appearance of multiple DNA fragments, the sum of which would present the total size of the RVFV insert. The recombinant plasmids depicted in FIG. 1 containing large RVFV DNA inserts were further studied. Restriction endonuclease site maps of the RVFV insert DNA of these plasmids were generated by standard procedures (Maniatis et al., 1982, Molecular Cloning, A Laboratory Manual, Cold Spring Harbor, NY). Selected restriction endonuclease sites are depicted in FIG. 1.

Figure 3A:
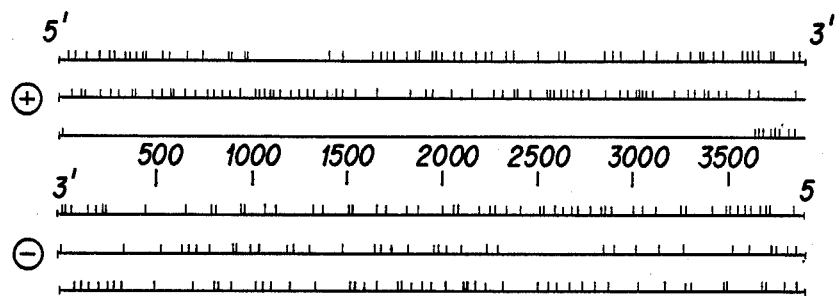

The recombinant plasmids derived from the cDNA clones were sequenced by the chemical sequencing method of Maxam and Gilbert (1980, Methods in Enzymology, Part I, Vol. 65: 499–560). The DNA sequence corresponding to the complete M RVFV RNA Sequence is depicted in FIG. 2. This sequence is presented in the positive polarity (complementary to the viral M RNA), and the deduced amino acid sequence of the major open reading frame is indicated. The results revealed that one end of our alignment possessed the phlebovirus common consensus sequence of (3')-UGUGUUUCUG... (Clerx-van Haastan et al., 1982, J. gen. Virol. 61: 289), and at the opposite end, the complementary (5') sequence (FIG. 3A). These data indicated that our composite cDNA inserts represented a complete copy of the M RNA segment. Subsequently the complete sequence of the segment of RVFV was determined. The genomic M RNA is 3884 nucleotides in length.

Figure 3B:
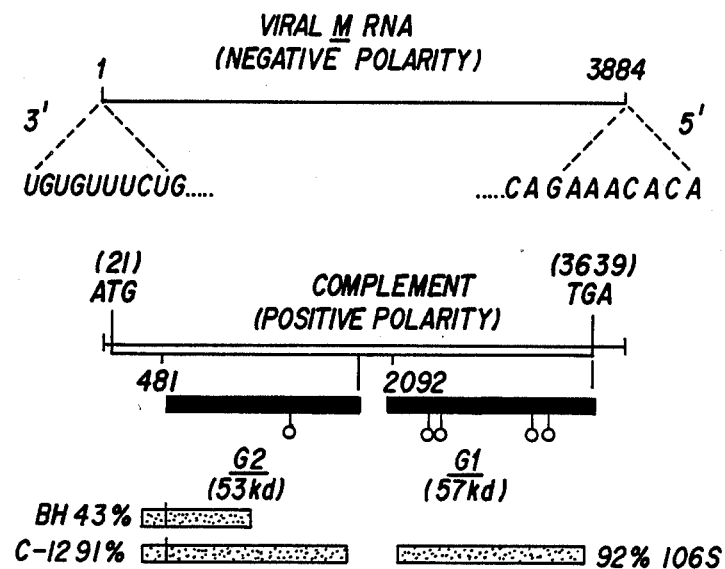

Analysis of the nucleotide sequence in all three reading frames of both sequence polarities for regions capable of encoding significant amounts of polypeptide revealed one major open reading frame (see FIG. 3A). This occurred in the positive polarity (complementary to the negative-sense viral M RNA), and was bounded at the amino end by a UAA codon at position 18 and a UGA codon at position 3639. The first initiation codon (AUG) was found at position 21. Thus the maximum coding potential of this single open reading frame was approximately 133 kd of protein. To definitively establish that the two RVFV glycoproteins, G1 and G2, were in fact encoded by the M RNA segment, the amino-terminal amino acid sequence of the G1 and G2 polypeptides isolated from highly purified virus preparations was determined. The resultant amino-terminal sequences of both RVFV glycoproteins were found within the deduced amino acid sequence of the major open reading frame (FIG. 3B). Although these data allowed the start positions of the mature viral proteins to be defined (position 481 for G2 and position 2092 for G1), the exact sites of termination could not be established in the absence of carboxy-terminal protein sequencing data on both proteins. However, by knowing these protein start positions, and by determining the apparent molecular weights of the nonglycosylated G1 and G2 proteins observed in virus-infected, tunicamycin-treated cells (57 kd and 53 kd, respectively), it is estimated that the G2 protein coding sequences terminate near position 1924, and those of the G1 polypeptide end at the termination codon at position 3639. Thus there appeared to be approximately 6 kd of coding information between G2 and G1 genes (FIG. 3B). Furthermore, there was protein coding information for about 17 kd of polypeptide before the start of the mature G2 protein sequences (FIG. 3B). The role of these coding sequences is unknown at present. They may encode previously unidentified (nonstructural) RVFV polypeptides, or they may be required for precursor (poly)protein processing and/or transport to and from the Golgi apparatus, where virus maturation occurs. Work is ongoing to address these possibilities.

From the deduced amino acid sequence of the G2 and G1 glycoproteins, their amino acid compositions have been determined. One striking feature of the composition of both proteins was their high cystein content (6% for G2 and 5% for G1). Analysis of their amino acid sequence for potential asparagine-linked glycosylation sequences (Asn-X-Ser/Thr) revealed in G2 only one site, near the middle of the polypeptide, and four potential sites in the G1 protein, two toward the $NH_2$-end and two toward the carboxy-end (FIG. 3B).

6.2.6. Construction of pRV51/134/106

The recombinant plasmid, pRV51/134/106, contains the entire RVFV sequence represented in cDNA clones pRV51, pRV134 and pRV106 arranged linearly and represents about 92% of the entire M RNA segment of the RVFV genome (see FIG. 1). The pRV51/134/106 was constructed by the ligation of three DNA fragments as follows:

(a) pRV51 was cleaved to completion using SphI (i.e., a unique site present in the $tet^r$ gene of the pBR322 portion of the plasmid). After partial restriction digestion using SstI (there are two SstI sites in pRV51; see FIG. 1) a 4260 b.p. DNA fragment encoding the carboxy portion of the $tet^r$ gene, a portion of pBR322 DNA and the amino coding terminus of the M RVFV (i.e., the 3' portion of the genomic M RVFV RNA) was purified by gel electrophoresis.

(b) pRV134 was cleaved to completion using HpaI (a unique restriction site in the RVFV sequence) and SstI (there are two SstI sites in pRV134; see FIG. 1) and a 948 b.p. DNA fragment encoding the central portion of the M RVFV sequence was purified by gel electrophoresis.

(c) pRV106 was cleaved to completion with HpaI (a unique site in the RVFV sequence) and SphI (a unique site present in the $tet^r$ gene of the pBR322 portion of the recombinant plasmid); the resultant 2780 b.p. DNA fragment encoding RVFV M sequences was purified by gel electrophoresis.

The three gel purified fragments obtained in (a), (b), and (c) above were ligated and used to transform *E. coli*. Tetracycline resistant transformants were isolated and restriction analysis of the recombinant plasmid designated p51/134/106 confirmed the structure depicted in FIG. 1.

6.3. Expression Cloning of RVFV Gene Sequences Derived from the Viral M RNA

Various portions of the RVFV DNA sequences derived from the cDNA clones described in Section 6.2. and depicted in FIG. 1 were inserted into expression vectors under the transcriptional control of the lac promoter or the tac promoter. The expression vectors containing the RVFV-specific sequences were manipulated so that the RVFV related polypeptides produced by *E. coli* transformants were: (1) cro/RVFV/β-gal fusion proteins comprising the amino terminus of cro fused to an RVFV related polypeptide which in turn is fused to β-galactosidase, and (2) cro/RVFV polypeptide comprising the amino terminus of cro fused to an RVFV related polypeptide (hereinafter referred to as unfused proteins).

Although the cro/RVFV/β-gal fusion proteins are easily assayed and detectable due to their enzymatic activities and high molecular weight (i.e., greater than about 140,000 daltons), the fusion proteins are not usually used as immunogens because they may be poorly immunogenic. The large (greater than 116,000 daltons) β-galactosidase portion of the fusion protein may interfere with the proper folding of the molecule which may be necessary for correct presentation of the antigenic determinants. Therefore, in some of the constructions described below the β-galactosidase sequences were removed and replaced with translational stop sequences and transcriptional attenuation sequences in order to direct host cell production of unfused RVFV polypeptides.

Figure 6A:
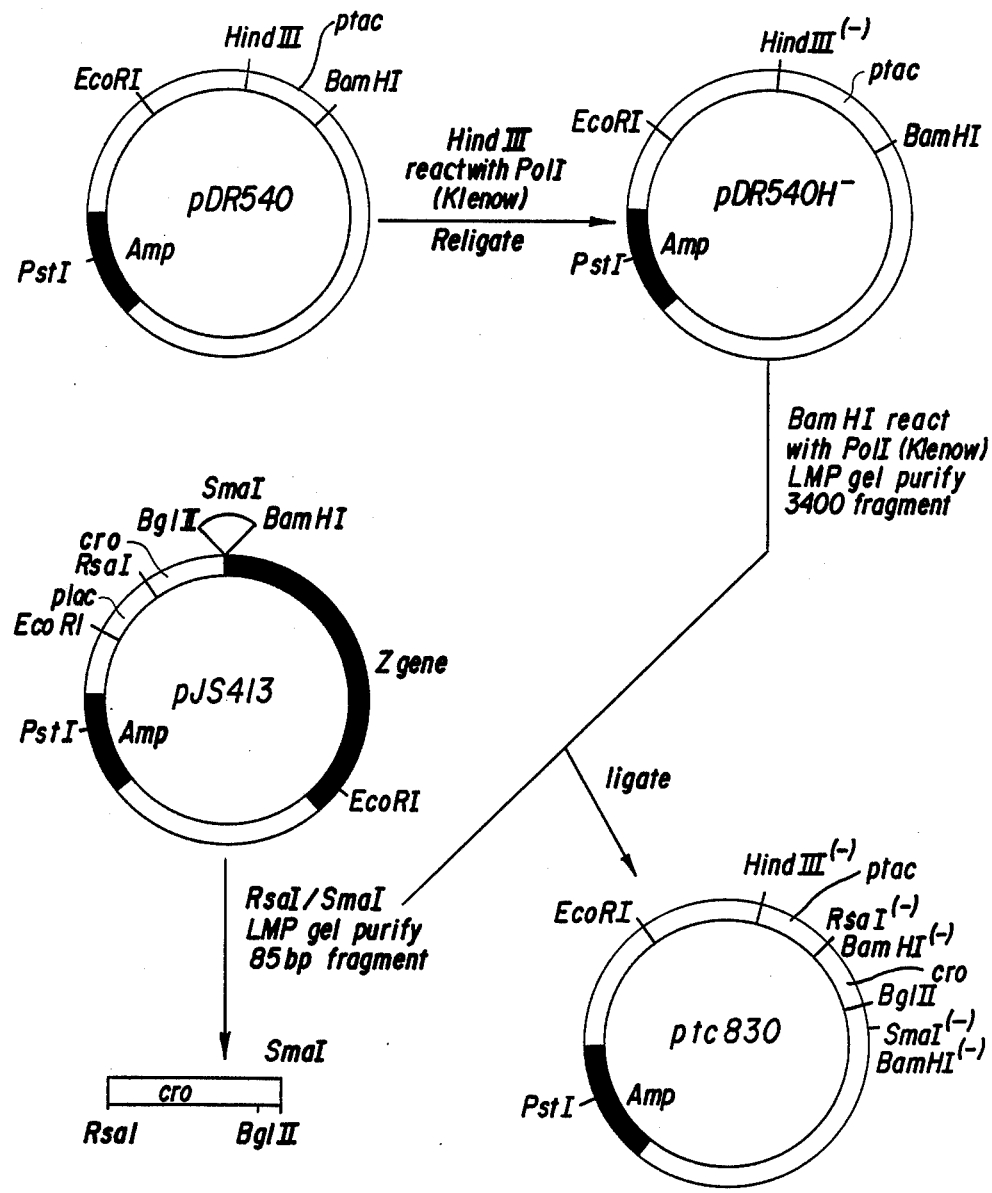
FIG. 6A (not drawn to scale) represents the construction of the tac promoter vector ptc830.
Figure 6B:
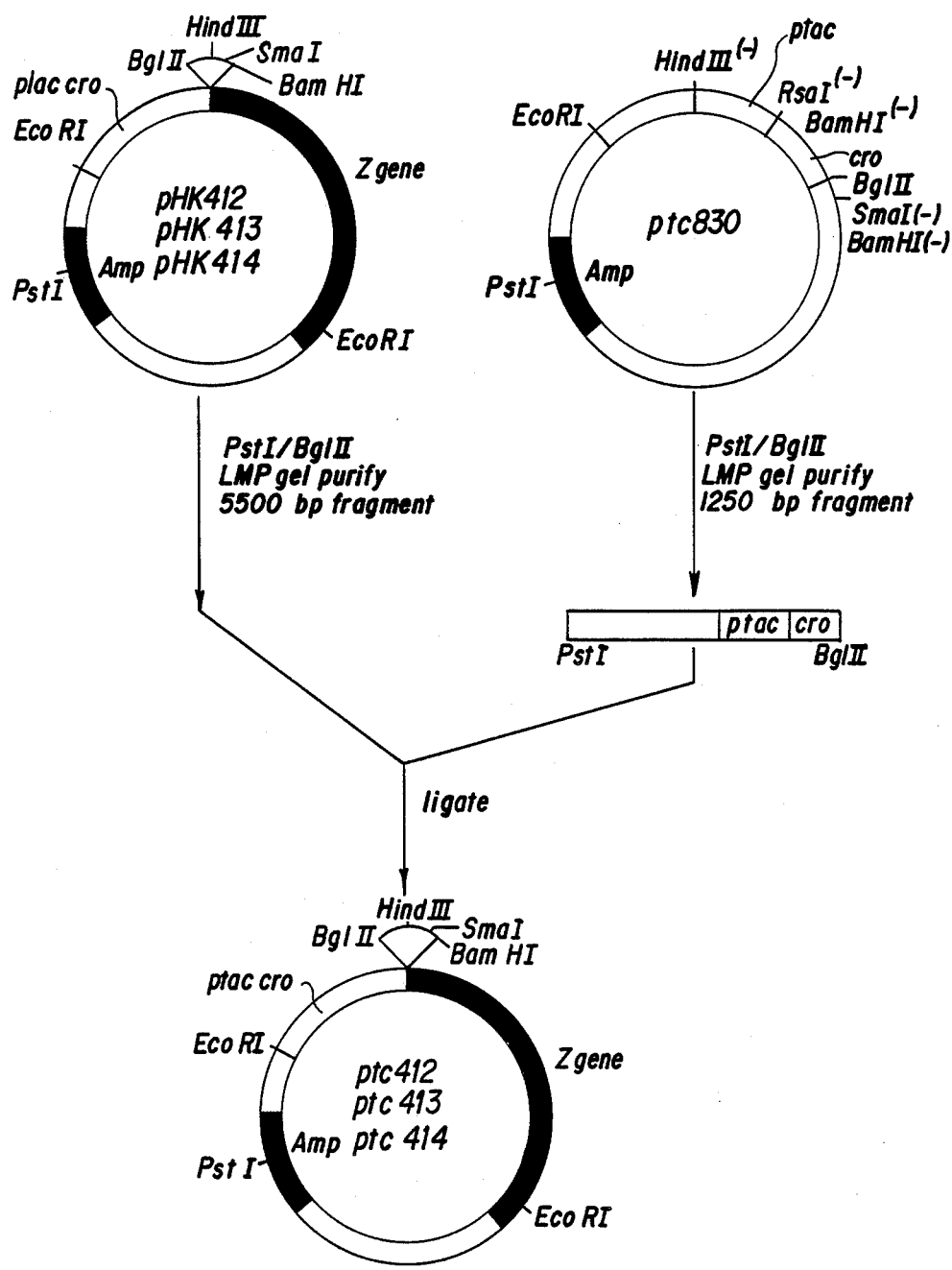
FIG. 6B (not drawn to scale) represents the construction of the tac promoter expression vectors ptc412, ptc413 and ptc414.
Figure 7:
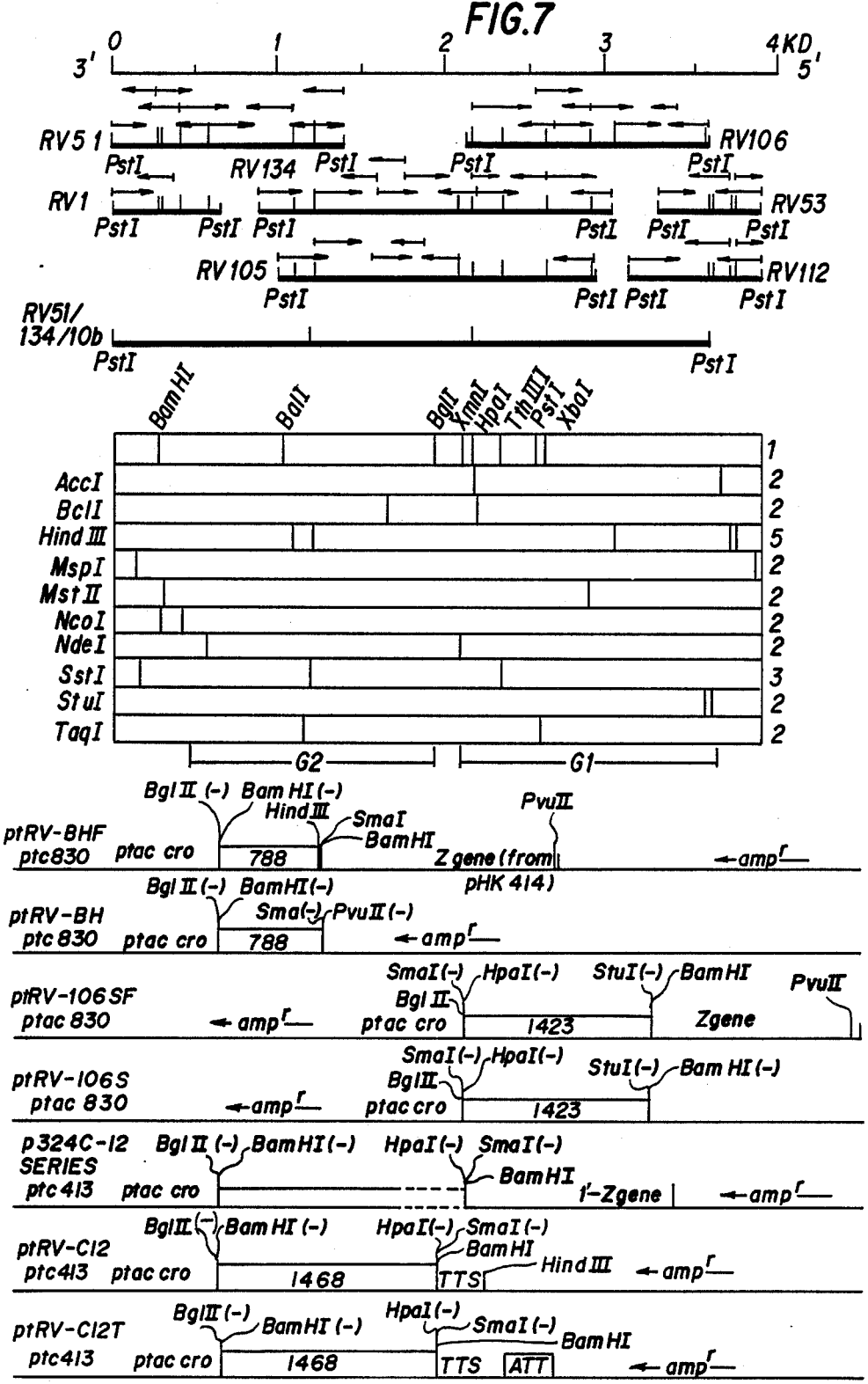
FIG. 7 (not drawn to scale) represents the construction of various recombinant plasmids derived from portions of the RVFV M nucleotide sequence and the E. coli tac promoter expression vectors. In the ptRV-C12 and ptRV-C12T constructions translational stop sequences are indicated as TTS and transcriptional attenuation sequences are indicated as ATT.

To aid in understanding the following subsections which describe the construction of these recombinants, each expression vector is depicted in FIGS. 4 and 6 and each recombinant molecule is represented in FIGS. 5 and 7. Within the text that follows, DNA fragments are identified according to their length in base pairs (b.p.) and according to their termini generated by restriction enzymes. The termini of each DNA fragment containing RVFV nucleotide sequences are indicated on either side of a slash in the order of the direction of transcription of the RVFV DNA sequence. For example, an 895 b.p. BamHI/SstI DNA fragment signifies a DNA fragment which has a BamHI cohesive end at its amino-coding terminus and an SstI cohesive end at its carboxy-coding terminus and is 895 nucleotides in length.

6.3.1. Expression Vectors Containing the lac Promoter: pHK414, pHK412, pHK411, pJS413 and pCJ423

The lac promoter expression vectors are depicted in FIG. 4 and described below.

The expression vector pJS413 (FIG. 4), is a pBR322 derivative which contains the $amp^r$ (β-lactamase) gene, a lac promoter (P lac), lac and cro ribosome binding sites ($SD^{lacZ}$ and $SD^{cro}$ are represented as "cro" in all figures), a chain initiation ATG with 69 nucleotides of cro (cro), and a modified β-galactosidase gene (the lac i-z gene, hereinafter referred to as the z-gene). Insertion of a gene in the correct reading frame between the cro initiation ATG of pJS413 and the z-gene allows for expression of a fusion protein in transformed cells. Between cro and β-galactosidase sequences, several restriction endonuclease sites are present to facilitate the insertion of DNA fragments for expression purposes (i.e., production of fusion protein). The restriction sites between cro and β-galactosidase in pJS413 are arranged as follows: cro-BglII-SmaI-BamHI-z.

The expression pHK414 is a pJS413 derivative. In fact, pHK414 contains all the elements of pJS413 but differs in its unique cloning sites across the cro-z junction. The cloning sites of pHK414 are: cro-BglII, HindIII, SmaI, BamHI-z. As in pJS413, the z-gene is not in phase with the cro ATG, thus, the intact plasmid does not direct the production of β-galactosidase. However, when a DNA fragment of the appropriate length (3n+2) is inserted into any of these cloning sites on the pHK414 plasmid, the reading frame of the z-gene is readjusted with respect to the cro ATG and, provided that the inserted DNA sequence contains no termination signals (e.g., TGA, TAA, or TAG) that are in phase with the cro ATG or z-gene, a β-galactosidase fusion protein will be produced by host cell transformants.

Expression vectors pHK412 and pHK413 are identical to pHK414, except for the translational reading frame phasing of the restriction sites between cro and β-galactosidase. A 3n DNA fragment readjusts the reading frame of pHK412; and a 3n+1 DNA fragment readjusts the reading frame of pKH413. Expression vector pHK411 is analogous to the above mentioned vectors except that the cloning sites of pHK411 have the following configuration: cro-BglII-HindIII-BamHl-Z. A 3n+1 DNA fragment readjusts the reading frame of pHK411.

Expression vector pCJ423 is arranged in a manner similar to pHK414, with the following exceptions. The β-lactamase gene has been replaced with the chloramphenicol inactivating gene, providing resistance to chloramphenicol (designated as "CAM" in FIG. 4). The restriction enzyme sites present between the cro and z gene sequences are arranged as follows: cro BglII-PstI-BamHI-z. Since the β-lactamase gene has been removed, along with its internal PstI restriction site, the PstI site present between the cro and z genes is unique in this plasmid.

6.3.2. Insertion of RVFV DNA Sequences Derived from the M RNA into the lac Promoter Expression Vectors Portions of the RVFV M RNA genetic sequences represented in plasmids pRV51, pRV134 and pRV106 were inserted into lac promoter expression vectors so as to express RVFV-related polypeptide sequences in *E. coli* transformants. For purposes of illustration, the constructions of seven expression plasmids are depicted in FIG. 5 and are described below.

pRVE451 pRVE451 was constructed by the ligation of an RVFV-specific DNA fragment derived from pRV51 into the cloning site of the expression vector pCJ423. A portion of RVFV M RNA sequences present in pRV51 were excised by digesting the plasmid with the restriction enzymes BamHI and PstI. This resulted in the generation of a BamHI/PstI RVFV-specific DNA fragment of 1040 b.p. This fragment was purified by electrophoresis in a LMP agarose gel. the expression vector pCJ423 (containing the chloramphenicol resistance gene) was restricted with the restriction enzymes BglII and PstI, and the linear vector backbone was also purified by low melting point agarose gel electrophoresis. These two DNA fragments (approximately 20 ng of each) were ligated in a 20 ul ligation reaction as described in Section 6.1.6. N.B., The BglII and BamHI single-stranded or staggered ends are complementary in base composition, and thus are compatible cohesive ends that will anneal and ligate. However, both the BglII and BamHI sites are destroyed after ligation because the resulting sequence is no longer recognized by either enzyme.

The ligation mixture was then used to transform competent *E. coli* strain NF1829. The *E. coli* strain NF1829 is a K-12 MC1000 derivative carrying an F'-lac episome with the lacIq mutation for lac repressor overproduction. Thus, in strain NF1829, the lac promoter must be induced in order to obtain expression of a gene inserted into the expression plasmid. The lacZ-gene encoding β-galactosidase present on the F'-lac episome is inactivated by a Tn5 (transposon) insertion. Chloramphenicol-resistant colonies were selected. Plasmid DNA from several of these chloramphenicol-resistant clones was isolated and subjected to restriction endonuclease analyses to confirm that the pRV51 BamHI-PstI 1040 b.p. RVFV DN fragment was properly inserted into the pCJ423 vector. One clone, designated pRVE451, was used for further analyses.

pRVE414-51 pRVE414-51 was constructed using similar methods. Plasmid pRV51 was digested with the restriction enzymes BamHI and HindIII. This resulted in a RVFV DNA fragment of 790 b.p. in length, which was subsequently purified by LMP agarose gel electrophoresis. The expression vector pHK414 was cleaved with the BglII and HindIII restriction enzymes, and the linear vector DNA was similarly gel-purified. Ligation and transformation proceeded as described above, and ampicillin-resistant bacterial colonies were selected. Restriction enzyme analyses of the plasmid DNA isolated from several of these ampicillin-resistant clones confirmed the proper insertion of the pRV51 BamHI-HindIII 790 b.p. RVFV DNA into the expression vector pHK414. One clone, designated pRVE414-51, was subsequently studied.

pCJRV134-P pCJRV134-P was constructed by the ligation of a RVFV-specific DNA fragment derived from pRV134 into the cloning site of the expression vector pCJ423. A portion of the RVFV M sequence present in pRV134 were excised by digesting the plasmid with the restriction enzyme PstI. This resulted in the generation of two RVFV-specific DNA fragments of 480 b.p. and 1660 b.p. The 480 b.p. RVFV DNA fragment was purified by gel electrophoresis in LMP agarose. The expression vector pCJ423 was cleaved with the PstI enzyme, and this linear DNA treated with bacterial alkaline phosphatase (BAP) in order to reduce the probability of plasmid-plasmid ligation as follows: PstI-cleaved pCJ423 DNA, present at 5 ug/ml, in 50 mM Tris-HCl, pH 8.5, was incubated at 37° C. for 1 hour with 1 unit/ml of the BAP enzyme (P.L. Biochemicals, Milwaukee, WI). One unit of BAP catalyzes the hydrolysis of 1 umole of p-nitrophenyl phosphate/minute at 25° C., pH 8.0. The BAP reaction was terminated by phenol extraction, and the DNA was recovered after ethanol precipitation. This DNA was then subjected to low-melting-point agarose gel electrophoresis, and the linear vector DNA was excised and then ligated with the RVFV 480 bp fragment derived from PstI cleavage of pRV134. Transformation of *E. coli* NF1829 proceeded as described above, and chloramphenicol-resistant bacterial colonies were selected. Restriction enzyme analysis of the plasmid DNA from several of these chloramphenicol-resistant clones confirmed the proper insertion of the pRV134 PstI-PstI 480 bp RVFV DNA into the expression vector pCJ423. One clone, designated pCJRV134-P, was subsequently studied.

pJSR134-HpX pJSR134-HpX was constructed in the following manner: pRV134 was digested with the restriction enzyme XbaI. The resultant 5'-cohesive ends of the enzyme cleavage site were made blunt by reaction with DNA polymerase I (Klenow fragment) as follows: to the XbaI restriction reaction mixture, containing 1 ug pf pRV134 in 30 ul, was added all four deoxyribonucleoside triphosphates (dNTPs: dCTP, dGTP, dATP, dTTP) to a final concentration of 50 uM. One unit of DNA polymerase (Klenow fragment, New England Biolabs, Beverly, MA) was added, and the mixture was incubated at 22° C. for 5 minutes. One unit is the amount of enzyme capable of converting 10 nmoles of deoxyribonucleotides to an acid insoluble form in 30 minutes at 37° C. The reaction was terminated by heating at 65° C. for 10 minutes. The restriction endonuclease HindIII was then added, resulting in the generation of a RVFV-specific 1395 b.p. DNA fragment, which was subsequently purified by LMP agarose gel electrophoresis. This 1395 b.p. RVFV DNA fragment was ligated to the plasmid vector pHK412, which had been previously digested with the HindIII and SmaI enzymes and gel purified. $E.$ $coli$ NF1829 was transformed with this ligation mixture and ampicillin-resistant bacteria were selected. Restriction enzyme analyses of the plasmid DNA from several of these ampicillin-resistant bacteria confirmed the expected insertion of the pRV134 HindIII-XbaI (blunt-ended) 1395 b.p. RVFV DNA into the vector pHK412. One representative of this intermediate construction was then cleaved with the HpaI and BamHI restriction enzymes. This resulted in the generation of a 466 b.p. RVFV-specific fragment containing the HpaI end from the RVFV sequences and the BamHI end derived from pHK412. This gel-purified fragment was then ligated to the expression vector pJS413 which had been previously restricted with the SmaI and BamHI enzymes and gel-purified. This ligated mixture was used to transform $E.$ $coli$ NF1829, and ampicillin-resistant colonies were selected. Restriction analyses of the plasmid DNA from several of these ampicillin-resistant clones revealed the proper insertion of the pRV-132 HpaI-XbaI 466 bp RVFV DNA into the expression vector pJS413. One clone, designed pJSR134-HpX, was used for subsequent study.

pRVE-BHpa-20 pRVE-BHpa-20 was constructed by the ligation of an RVFV-specific DNA fragment derived from pRV51 into the cloning site of the expression vector pHK413. The plasmid pRV51 was digested with BamHI and SstI. An 895 b.p. BamHI/SstI RVFV-related DNA fragment was isolated by gel electrophoresis in LMP agarose. The expression vector pHK413 was digested with BglII and SmaI (which creates a BglII cohesive end and a SmaI blunt end) and the linear backbone was also purified by gel electrophoresis in LMP agarose. The 895 b.p. BamHI/SstI RVFV-related DNA fragment was ligated to the BglII/SmaI blunt ended pHK413. As explained earlier, the BglII and BamHI staggered ends are complementary and therefore will anneal and ligate. In addition, the SmaI blunt end of the vector will ligate to the 3'-staggered end of the SstI site of the 895 b.p. RVFV-related DNA fragment. However, both the BamHI and BglII sites and both the SmaI and SstI sites are destroyed after ligation (i.e., the sequences resulting from ligation are no longer recognized by the enzymes). The ligation mixture was used to transform $E.$ $coli$ NF1829.

pHKRV106 pHKRV106 was constructed by the ligation of three DNA fragments as described below:

(a) pRV106 was digested with SstI and HindIII and a 683 b.p. SstI/HindIII DNA fragment containing RVFV specific DNA sequences was purified by gel electrophoresis in LMP agarose.

(b) pJSRV134-HpX was digested with PstI and SstI and a 1405 b.p. PstI/SstI DNA fragment encoding the amino coding portion of the $amp^r$ gene, the plac, cro ribosome binding sties, and a portion of the RVFV-specific DNA sequence was purified by gel electrophoresis in LMP agarose.

(c) pHK411 was digested with HindIII and PstI and a 5500 b.p. HindIII/PstI DNA fragment encoding the z-gene (for $\beta$-galactosidase) and the carboxy coding portion of the $amp^r$ gene was purified by gel electrophoresis in LPM agarose gel.

The three fragments prepared above in (a), (b), and (c), i.e., the 1405 b.p. PstI/SstI pJSRV134-HpX DNA fragment, the 683 b.p. SstI/HindIII pRV106 DNA fragment, and the 5500 b.p. HindIII/PstI pHK411 DNA fragment were ligated and transformed into $E.$ $coli$ NF1829. Ampicillin resistant colonies were selected and the correct construction of pHKRV106 was confirmed by restriction analysis.

pHKRV106St pHKRV106St was constructed by the ligation of an RVFV-specific DNA fragment derived from pRV106 to pHKRV106. pRV106 was digested to completion with HindIII and StuI, and a 549 b.p. HindIII/StuI (blunt ended) DNA fragment encoding RVFV sequences was purified by gel electrophoresis in LMP agarose. The recombinant expression plasmid pHKRV106 was digested with BamHI and the resulting BamHI cohesive ends were filled in using the Klenow fragment of DNA polymeraseI in order to create blunt ends (as a result, the BamHI sequence is converted from GGATCC to GATCC). Subsequently the cleaved pHKRV106 was digested with HindIII and 6500 b.p. BamHI(−) blunt ended/HindII DNA backbone encoding the z-gene (for $\beta$-galactosidase), the $amp^r$ gene, plac, the cro ribosome binding sites and an RVFV-specific DNA sequence was purified by gel electrophoresis in LMP agarose. The 6500 b.p. BamHI(−) blunt ended/HindIII pHKRV106 DNA fragment and the 549 b.p. HindIII/blunt ended StuI pRV106 DNA fragment were ligated and used to transform $E.$ $coli$ NF1829. N.B., the StuI blunt end of the 549 b.p. DNA fragment will ligate to the BamHI(−) blunt end of the vector, however, after ligation the StuI recognition sequence is restored. This occurs because the terminal nucleotide of the cleaved StuI sequence is a guanine (G) which restores the first G of the BamHI recognition sequence (GGATTCC) in the ligated plasmid.

6.3.3. Expression Vectors Containing the tac Promoter: ptc412, ptc413 and ptc414

Various tac (i.e., trp-lac) promoter/operator region expressions vectors were constructed. The hybrid promoter was constructed by combining the 35 region and the 10 region (the sequences which are the RNA polymerase binding site) of the tryptophan and the lactose promoters.

The expression vector ptc830 contains cro sequences ligated to the strong tac promoter and was constructed as described below and in FIG. 6B. pDR540 (Russel, D. R., and Bennet, G. M., 1982, Gene 20: 231 was digested with HindIII and the resultant 5' cohesive ends were made blunt with the Klenow fragment of DNA polymerase I. The blunt ended fragments were then religated and plasmid pDR540H- was isolated. This plasmid was digested with BamHI and the 5' cohesive ends from the restriction were made blunt with the Klenow fragment of DNA polymerase I and the linear backbone was purified in LMP agarose by gel electrophoresis. pJS413 was digested at a RsaI site upstream from the cro-sequence and at the unique SmaI cloning site. The resulting 85 b.p. fragment was then purified by polyacrylaminde gel electrophoresis and ligated to the gel purified pDR540H(−). The ligation mixture was transformed into E. coli NF1829 and ampicillin resistant colonies selected. Insertion of the cro sequences from pJS413 was confirmed by restriction analysis. One clone, designated ptc830 was selected.

Plasmid ptc830 was used as source of the modified tac promoter for the construction of the ptac containing plasmids described below.

The expression vectors ptc412, ptc413 and ptc414 are derivatives of pHK412, pHK413 and pHK414, respectively and contain the tac promoter from ptc830. The construction of ptc412 is described below and is shown in FIG. 6B. The construction of the expression vector ptc413 and ptc414 is identical to that for construction of ptc412 and is also shown in FIG. 6B. ptc830 was digested with PstI and BglII and the 1250 b.p. fragment containing the tac promoter was isolated by LMP gel eletrophoresis. pHK412 was also digested with BglII and PstI and the 5500 b.p. fragment containing the β-galactosidase gene was isolated by LMP gel electrophoresis. These two fragments were ligated and transformed into E. coli NF1829. Ampicillin resistant bacterial colonies were selected and the proper construction was confirmed by restriction analysis.

6.3.4 Insertion of RVFV DNA Sequences Derived from the M RNA into the tac Promoter Expression Vectors Portions of the RVFV M RNA genetic sequences represented in plasmids pRV51, pHKRV106, and pRV51/134/106 were inserted into tac promoter expression vectors to express RVFV-related polypeptide sequences in E. coli transformants. For purposes of illustration, the constructions of the tac expression plasmids are depicted in FIG. 7 and are described.

ptRV-BHF ptRV-BHF was constructed by the ligation of three DNA fragments as described below.

(a) ptc830 was digested with PstI and BglII. A 1250 b.p. PstI/BglII DNA fragment encoding the amino terminus of the amp$^r$ gene, ptac, and the cro ribosome binding sites was purified by gel electrophoresis in LMP agarose.

(b) pRV51 was digested with BamHI and HindIII. An 788 b.p. BamHI/HindIII DNA fragment encoding an RVFV sequence was purified by gel electrophoresis in LMP agarose.

(c) pHK414 was digested with PstI and HindIII. A 5500 b.p. HindIII/PstI DNA fragment encoding the z gene and the carboxy terminus of the amp$^r$ gene was purified by gel electrophoresis in LMP agarose.

The three DNA fragments prepared in (a), (b) and (c) above, i.e., the 1250 b.p. PstI/BglII ptRV-BHF DNA fragment, the 788 b.p. BamHI/HindIII pRV51 DNA fragment and the HindIII/PstI pHK414 DNA fragment were ligated and used to transform E. coli NF1829. The proper constructions were confirmed by restriction analysis of the plasmids isolated from ampicillin resistant colonies.

ptRV-BH ptRV-BH was constructed by removing the β-galactosidase z gene from plasmid ptRV-BHF. ptRV-BH was digested with SmaI and PvuII. A 4250 b.p. DNA fragment encoding an RVFV sequence was purified in LMP agarose. The 4250 b.p. fragment was ligated to itself and used to transform E. coli SK107 F'iq (gal−, lac−, mal−, mtl−, rho−, xyl−, leu−, thr−, thi−, rpst−, rna-19, pnp-7; the F factor plasmid carries on it the i$^q$ mutation which leads to the overproduction of the lac repressor protein). The proper construction was confirmed by restriction analysis of the plasmids isolated from ampicillin resistant colonies.

ptRV-106SF ptRV-106SF was constructed by the ligation of two DNA fragments as described below.

(a) pHKRV106St was digested with BglII and XmnI. An 8000 b.p. BglII/XmnI DNA fragment encoding an RVFV sequence, the z gene and the carboxy terminus of the amp$^r$ gene was purified by gel electrophoresis in LMP agarose.

(b) ptc830 was digested with XmnI and BglII. A 900 b.p. DNA fragment encoding the amino terminus of the amp$^r$ gene, ptac, and the cro ribosome binding sites was purified by gel electrophoresis in LMP agarose.

The two fragments prepared in (a) and (b) above, i.e., the 8000 b.p. BglII/XmnII pHKRV106St and the 900 b.p. XmnI/BglII were ligated and used to transform E. coli NF1829. The proper constructions were confirmed by restriction analysis of the plasmids isolated from ampicillin resistant colonies. ptRV-106S ptRV-106S was constructed by removing the β-galactosidase gene from ptRV106SF. ptRV106SF was digested with BamHI. The resultant 5' cohesive ends were made blunt ended by reaction with the Klenow fragment of DNA polymerase I and subsequently digested with PvuII. The 4500 b.p. DNA fragment containing an RVFV sequence was purified in LMP agarose by gel electrophoresis. The fragment was ligated to itself and used to transform E. coli SK107 F'iq. The proper construction was confirmed by restriction analysis of the plasmids isolated from ampicillin resistant colonies.

p324-C12 Series

A series of plasmids containing portions of the G2 gene of RVFV were constructed by the following procedures.

pRV51/134/106 was digested with HpaI which cleaves at a unique site approximately 225 b.p. 3' to the carboxy terminus of the G2 gene. This fragment was purified by gel electrophoresis in LMP agarose. To remove the various DNA sequences 3' to the carboxy terminus of the G2 gene, 2.0 ug of the HpaI linearized plasmid was digested with 0.5 units of nuclease Bal 31 in 12 mM CaCl$_2$, 12 mM MgCl$_2$, 20 mM tris-HCl, pH 8.0, 1.0 mM EDTA and 0.6M NaCl in a total reaction volume of 50 ul and the mixture was incubated at 30° C. 12.5 ul fractions were removed at 2, 4, 6, and 8 minute time points after the addition of enzyme, phenol extracted and finally ethanol precipitated. Individual samples were digested to completion with BamHI and DNA fragments were separated in 1% LMP agarose by gel electrophoresis. DNA fragments of approximately 1600 b.p., encoding G2 DNA were isolated and purified. The expression vector pTC413 was digested with BglII and SmaI and the approximately 6800 b.p. backbone was isolated and purified by gel electrophoresis in LMP agarose.

The 1600 b.p. BamHI variable blunt ended G2 DNA fragments were ligated to the BglII/SmaI backbone of TC413 using T4-DNA ligase. The ligation mixture was used to transform *E. coli* strain NF1829 and plated onto LB agar plates containing 100 ug/ml of ampicillin. Individual colonies were selected and screened for the presence of the G2 genome by DNA colony hybridization as described supra. The size of the RVFV-G2 insert from positive clones was determined and several colonies containing the largest inserts including p323C-19, p324C-4, and p324-C12 were isolated.

ptRV-C12 ptRV-C12 was constructed by removing the β-galactosidase gene from p324-C12 and inserting a DNA sequence encoding three translational stop sequences in tandem. p324-C12 was digested with PstI and BamHI. A PstI/BamHI DNA fragment approximately 2718 b.p. long encoding the amino terminus of the amp$^r$ gene, the tac promoter, cro ribosome binding sites and RVFV M RNA specific sequences was purified by gel eletrophoresis in LMP agarose. p288Ba is an expression vector which encodes three translational stop codons in tandem which are bounded by BamHI and HindIII restriction sites (i.e., BamHI-TAG-TAA-TGA-HindIII). p288Ba was digested with BamHI and PstI and a 2400 b.p. BamHI/PstI DNA fragment encoding the triple translational stop sequences (TTS), the origin of replication of pBR322 and the carboxy coding terminus of the amp$^r$ gene was purified by electrophoresis in LMP agarose.

The 2718 b.p. PstI/BamHI p324-C12 DNA fragment was ligated to the 2400 b.p. BamHI/PstI p288Ba DNA fragment. The ligation mixture was used to transform *E. coli* SK107'iq. Ampicillin resistant colonies were selected and the plasmid construction was verified by restriction analysis.

ptRV-C12T ptRV-C12T was constructed by removing the β-galactosidase sequences from plasmid p324-C12. p324-C12 was digested with PstI which cleaves in the β-lactamase gene and BamHI which cleaves at the G2-β-galactosidase junction. An approximately 2400 b.p. fragment encoding a portion of the bla gene, the tac promoter and cro-G2 gene sequences was isolated and purified by gel electrophoresis in LMP agarose. Plasmid p346-2 which contains a triple translational stop sequence (TTS) followed by the transcriptional termination sequences (indicated by ATT, or transcriptional attenuator sequences) of T1 (from the rrnB operon) was digested with PstI and BamHI. An approximately 2400 b.p. backbone DNA fragment encoding a portion of the bla gene, the ColE1 origin of replication, and the translational and transcriptional stop sequences was isolated and purified by gel electrophoresis in LMP agarose. The PstI/BamHI fragment from p324C12 and the PstI/BamHI fragment from p346-2 were ligated and used to transform *E. coli* SK107F'.

6.3.5. Identification of Transformants that Express RVFV Genetic Sequences as Protein To determine if the constructed recombinant expression plasmids containing RVFV gene sequences were capable of synthesizing the predicted cro/RVFV/β-galactosidase fusion proteins, or the cro/RVFV nonfusion proteins, total *E. coli* proteins from cells harboring these expression plasmids were analyzed by SDS-polyacrylamide gel electrophoresis, followed by Coomassie Brilliant Blue staining. For example, *E. coli*, transformed with one of the recombinant expression plasmids described above were grown in L broth nutrient medium in the absence or presence of inducer (1% lactose or 1 mM IPTG). Overnight cultures were harvested, lysed directly in SDS-gel sample buffer (2X sample buffer: 0.14M Tris-HCl, pH 6.8, 0.02% bromophenol blue, 22% glycerol, 6% SDS, 10% β-ME) by boiling for 5 minutes, and aliquots were subjected to SDS-polyacrylamide gel electrophoresis. All transformants containing the β-galactosidase gene ligated to RVFV sequences synthesized high molecular weight polypeptides only upon induction of the promoter. The large proteins are of the size predicted for fusion proteins based upon data relating to the size of the inserted RVFV DNA sequences and the Z gene. The molecular weights of the various fusion and non-fusion proteins produced are listed below:

| | Protein Produced by Transformant | |
|---|---|---|
| Plasmid | Molecular Weight (daltons) | % of Total Cell Protein |
| pRVE451 | 153,000 | 5–10 |
| pRVE414-51 | 142,000 | 5–10 |
| PCJRV134-P | 129,000 | 5–10 |
| pJSRV-134HpX | 132,000 | 15 |
| pRVE—BHpa-20 | 150,000 | 20 |
| pHKRV106 | 148,000 | 15 |
| pHKRV106St | 167,000 | 10 |
| ptRV—BH | 146,000 | 15 |
| ptRV—BH | 33,000 | 10 |
| ptRV106SF | 167,000 | 10 |
| ptRV106S | 57,000 | 10 |
| p323-19 | 174,000 | 3 or less |
| p324-C12 | 172,000 | 10–15 |
| p324-C4 | 180,000 | 3 or less |
| ptRV—C12 | 55,000 | 3 or less |
| ptRV—C12T | 50,000 | 5–10 |

6.4 Immunologic Characterization of the RVFV-Related Proteins Expressed in *E. coli*

To determine whether bacterially-produced polypeptides containing RVFV-derived sequences might be useful as potential immunogens in vaccine formulations and/or in diagnostic assays for RVFV, certain immunologic features of these proteins must be established. These polypeptides must contain immunologically relevant regions such that: (i) antibodies known to react with the authentic viral proteins react with the bacterially-produced polypeptides, and/or (ii) the bacterially-produced polypeptide themselves are capable of eliciting an appropriate immune response against the authentic virus or viral components when injected into animals. In other words, the RVFV fusion proteins should be (i) antigenic, and (ii) immunogenic.

6.4.1. Antigenicity of RVFV-Related Proteins Expressed in *E. coli*

To determine whether the RVFV sequences expressed in the *E. coli* transformants described above, contained antigenic determinants recognized by antibodies directed against authentic RVFV proteins, the bacterially produced RVFV-related proteins were radiolabeled with $^{35}$S-methionine and analyzed by immunoprecipitation and SDS-polyacrylamide gel electrophoresis and by Western blotting procedures.

Cell-free lysates of transformants were prepared as follows: 1 ml cultures of transformants were induced to produce their cro/RVFV/β-galactosidase fusion proteins or cro/RVFV proteins by the addition of IPTG (1 mM). After 30 minutes of growth at 37° C., [$^{35}$S]-methionine (100 uCi/ml; New England Nuclear, Boston, MA) was added for a brief period (1–5 minutes). The bacteria were then centrifuged from the culture medium, resuspended in 50 ul of 10 mM Tris-HCl (pH 7.4), 10 mM EDTA, to which 50 ul of 10 mg/ml lysozyme was added. After 15 minutes at 4° C., 0.9 ml of RIPA buffer (150 mM NaCl, 10 mM Tris-HCl, pH 7.4, 1% Triton X-100, 1% deoxycholate, 0.1% SDS) was added and the mixture was briefly sonicated. Cell debris was removed by centrifugation (16,000×g for 10 minutes), and the resulting cell-free lysate was used for immunoprecipitation.

Equal aliquots of the [$^{35}$S]-methionine-labeled bacterial lysates were incubated at 4° C. with 2 ul of the various antisera (described below). The immunoadsorbent Pansorbin (formalin-fixed, heat-killed, protein A-containing *Staphylococcus aureus* cells; Calbiochem-Behring, Corp., La Jolla, CA) was added (50 ul of a 10% solution) and after 10 minutes at 4° C., the antigen-antibody complexes were collected by centrifugation. The pellets were washed once with 1M buffer (1M NaCl, 10 mM Tris-HCl, pH 7.2, 0.1% NP-40), twice with RIPA buffer, and then resuspended in 50 ul of SDS-gel sample buffer (70 mM Tris-HCl, pH 6.8, 11% glycerol, 3% SDS, 5% β-ME, 0.01% bromophenol blue). After boiling for 1 minute, the immunoadsorbent was removed by centrifugation, and the released [$^{35}$S]-methionine-labeled proteins present in the supernatant were subjected to SDS-polyacrylamide gel electrophoresis (Laemmli, 1970, Nature 227: 680). The gel was fluorographed (Chamberlain, 1979, Anal. Biochem. 98: 132) and exposed to X-ray film.

Four sera were employed to determine antigenicity of the proteins produced by the pRVE-451 or pRVE414-51 transformants: normal guinea pig serum (N); guinea pig serum from an animal hyperimmunized with whole RVFV (anti-RV); guinea pig serum from an animal injected with partially purified RVFV glycoprotein G1 (anti-G1), and guinea pig serum from an animal injected with partially purified RVFV glycoprotein G2 (anti-G-2). The latter three sera were provided by Dr. J. Dalrymple, Department of the Army, USAMRIID, Ft. Detrick, Frederick, MD and his co-workers. The anti-RV serum recognizes principally the viral nucleocapsid protein and the two major surface glycoproteins G1 and G2. Serum anti-G1 recognizes principally the viral glycoprotein G1. However it does contain a very small amount of antibody to glycoprotein G2, due to a minor amount of contamination present in the partially purified protein preparation used to immunize the guinea pig. Similarly, serum anti-G2, in addition to the principle antibody response to glycoprotein G2, contains a minor amount of antibodies directed toward glycoprotein G1. None of these sera contained any antibody activity toward the unfused β-galactosidase protein as demonstrated by ELISA techniques, immunoprecipitation, and competition-immunoprecipitation experiments.

The immunoprecipitation results demonstrated that the pRVE-451 and pRVE-414-51 fusion proteins were specifically immunoprecipitated with antisera raised against authentic RVFV proteins. Furthermore, the results suggested that the expressed pRVE-451 and pRVE-414-52 sequences are most likely related to the RVFV glycoprotein G2. Thus these bacterially-produced RVFV polypeptides clearly possess RVFV-specific antigenic determinants.

Five antibody preparations were employed to determine antigenicity of proteins produced by ptRV-BH or ptRV-106S transformants: normal guinea pig serum (N); guinea pig serum from an animal hyperimmunized with whole RVFV (anti-RV); and monoclonal antibodies (produced by mouse hybridoma cells) specific for either glycoprotein G1 (monoclonal anti-G1) or glycoprotein G2 (monoclonal anti-G2) or an unrelated protein, (monoclonal anti-N). The anti-RV, anti-G1 and anti-G2 were provided by Dr. J. Dalrymple, Department of the Army, USAMRIID, Ft. Detrick, Frederick, MD and his co-workers. As explained above, the anti-RV serum recognizes principally the viral nucleocapsid protein and the two major surface glycoproteins G1 and G2. The immunoprecipitation results (see FIG. 8) demonstrated that RVFV polypeptides produced by ptRV-BH transformants or ptRV-106S transformants clearly possessed RVFV-specific antigenic determinants. For example, the ptRV-BH polypeptide is very avidly recognized by the anti-G1 monoclonal antibody and barely detected by the anti-RV serum; the anti-N serum (i.e., antiserum directed against a protein unrelated to G1 or G2 of RVFV) failed to immunoprecipitate the ptRV-BH protein. The ptRV-106S protein was very specifically recognized by both the anti-RV serum and the anti-G1 monoclonal antibody; the anti-G2 monoclonal antibody and anti-N failed to immunoprecipitate the polypeptide. Similar results were obtained with polypeptides expressed in other transformants.

6.4.2. Immunogenicity of RVFV-Related Proteins Expressed in *E. Coli*

To determine if the RVFV bacterial fusion proteins were able to elicit RVFV-specific immune responses when injected into animals (i.e., to act as immunogens), various formulations containing the RVFV related fusion proteins and unfused proteins were prepared and injected into laboratory mice. After an appropriate period of time, sera were obtained from the injected animals and evaluated for antibodies directed against authentic RVFV proteins by immunoprecipitation and SDS-polyacrylamide gel electrophoresis.

For the purposes of illustration, the procedures, methods, and results from the immunogenicity testing of the protein produced by pRVE414-51, ptRV-BH, or ptRV-106S will be described. Similar procedures have been used, and similar results have been obtained, employing the proteins obtained from the other transformants described supra. It should be recognized that many related or alternative procedures and methods may be employed to prepare proteins for immunizations and to evaluate immunogenicity. The following serves as one example of one embodiment of the invention.

A 500 ml culture of an *E. coli* transformant in LB supplemented with 1% lactose and 100 ug/ml ampicillin was grown overnight at 37° C. Cells were harvested by centrifugation, frozen at −70° C., and thawed in 25 ml of STE (0.01M Tris-HCl, pH 7.2, 150 mM NaCl, 1 mM EDTa). Lysozyme (8 mg) was added, and after 20 minutes at 4° C., Triton X-100 was added to a final concentration of 1%. This mixture was sonicated (20-15 second pulses in a Branson cell disruptor 350; Branson Sonic Power Co., Donberry, CT) and then layered onto 7 ml of a solution composed of 35% sucrose, 0.5% Triton X-100 in STE buffer in a polyallomer centrifuge tube. After centrifugation at 4° C. in an SW28 rotor (Beckman Instruments, Fullerton, CA) at 19,000 rpm for 60 minutes, the tube was drained, and the pelletted material was resuspended in 10 ml of STE. This slurry was then centrifuged at 16,000×g for 30 minutes and the resultant pellet was resuspended in 10 ml of water. SDS-polyacrylamide gel analysis of material prepared in this fashion indicated that the fusion protein was approximately 30-60% pure. The yield of pRVE414-51 fusion protein in this preparation was 150 mg. The yield for the ptRV-BH and ptRV-106S proteins were approximately 40 mg and 30 mg, respectively.

One means of preparing a pRVE414-51 immunogen is as follows: a portion of the partially purified fusion protein prepared as described above was adjusted to 50 mM NaOH, incubated at 65° C. for 5 minutes and then neutralized with 1M Tris-HCl, pH 6.8. This solution was then mixed with aluminium hydroxide (Rehsorptar, Reheis Chemical Comp, Berkeley HTs, NJ) in an amount corresponding to three times the amount of fusion protein present (weight/weight basis). After vigorous mixing, this slurry (in an amount corresponding to approximately 1 mg of fusion protein/3 mg of aluminium hydroxide per animal) was injected intramuscularly in mice. A second injection of one-half this amount was performed 21 days after the first injection. Animals were bled 7 days later and sera prepared.

One means of preparing ptRV-BH and ptRV-106S unfused proteins as immunogens is as follows: crude insoluble protein at a concentration of between about 5 and 40 mg/ml (containing 30-50% RVFV related proteins) were denatured and reduced using a buffer comprising 1% SDS, 5% β-mercaptoethanol, 50 mM Tris-HCl (pH 8.5) heated at 90°-100° C. for 2-10 minutes, cooled and dialyzed extensively against 50 mM Tris-HCl (pH 8.5), 10% sucrose, 0.2% β-mercaptoethanol. (Other denaturants which may be used include but are not limited to 8M urea, 6M guanidine-HCl; other reducing agents which may be used include but are not limited to 10-20 mM DTT, cysteine, or other reductant or various buffering systems preferably at the alkaline pH range.) The dialyzed preparations were formulated at a final dose concentration of from about 100 ug to about 1 mg with various adjuvants including aluminum hydroxide, Freund's incomplete adjuvant, L121 (a pluronic polyol glycol). The mice were injected intramuscularly as described above, boosted on day 21 and bled on day 28.

To test these sera for the presence of antibodies directed against authentic RVFV proteins, an [$^{35}$S]-methionine-labeled lysate of RVFV-infected Vero cells was prepared for use in an immunoprecipitation experiment. Vero cells, infected with RVFV and radiolabeled with 100 uCi [$^{35}$S]-methionine for 2 hours at approximately 14 hours post infection. The cells were harvested, pelletted, and then resuspended in lysis buffer (500 mM Tris-HCl, pH 7.2, 1 mM EDTA, 1% NP-40, 0.5% deoxycholate). Cell debris was removed by centrifugation at 100,000×g for 30 minutes at 4° C. Portions of this cleared lysate were incubated with various sera and processed in a manner similar to that described for immunoprecipitation, SDS-polyacrylamide gel electrophoresis, and fluorography in Section 6.4.1. More specifically, the cell lysates were immunoprecipitated with: normal guinea pig serum (Ngp); guinea pig antiserum directed against whole RVFV (anti-RVFV); normal mouse serum (Nmo); monoclonal antibodies directed against either authentic viral G1 glycoprotein (MAbanti-G1) or authentic viral G2 glycoprotein (MAbanti-G2) or mouse antiserum directed against the relevant bacterially produced RVFV related protein. The resultant immunoprecipitated proteins were subjected to electrophoresis in an SDS-10% polyacrylamide gel and subsequently fluorographed.

Serum obtained from an animal immunized with the pRVE414-51 fusion protein appeared to specifically immunoprecipitate a protein from RVFV-infected cell lysates that co-migrated with authentic RVFV glycoprotein G2. This result is consistent with, and supportive of, the antigenicity results described in Section 6.4.1., and clearly serves to demonstrate that the bacterially-produced RVFV peptide sequences are immunogenic.

Similarly, serum obtained from a mouse immunized with the unfused ptRV-BH protein specifically immunoprecipitated authentic G2 glycoprotein, and serum obtained from a mouse immunized with unfused ptRV-106S protein specifically immunoprecipitated authentic G1 glycoprotein.

In addition, these bacterially produced RVFV proteins were able to elicit virus neutralizing antibodies in mice. Virus neutralizing antibodies were measured in a standard plaque-reduction neutralization (PRN) assay in which the serum titer was measured as the reciprocal of the highest dilution reducing the number of RVFV induced plaques by 80% (Eddy et al., 1981, in Contributions to Epidemiology and Biostatistics, Vol. 3. Rift Valley Fever; T. A. Swartz, M. A. Klingsburg, and N. Goldblum, eds; pp. 124–141, Karger, Basel). To date, ptRV-BH has been most extensively studied. We have been able to routinely elicit PRN titers of 20–40 in mice. Titers of 10–40 have been shown to protect mice, hamsters and rats from lethal RVFV challenge (Eddy et al. ibid).

The foregoing results indicate that bacterially produced cro/RVFV/β-galactosidase fusion proteins and unfused cro/RVFV proteins possess antigenic determinants capable of being recognized by antisera containing virus neutralizing antibodies to RVFV, and further demonstrate that these proteins are able to elicit a RVFV-specific immune response in animals when such proteins are used as immunogens. Furthermore, the elicited immune response proved to be specifically virus neutralizing antibodies. The ability to use the RVFV-related proteins described herein as immunogens capable of eliciting an RVFV neutralizing immune response demonstrates the utility of these RVFV-related proteins in vaccines which can protect the host against RVF disease.

7. DEPOSIT OF MICROORGANISMS

It is to be understood that all base pair sizes given for nucleotide sequences are approximate and are used for purposes of description. Furthermore, it is apparent that many modifications and variations of this invention as hereinbefore set forth may be made without departing from the spirit and scope thereof. The specific embodiments described are given by way of example only and the invention is limited only by the appended claims.

The following *E. coli* strains carrying the listed plasmids have been deposited with the Agricultural Research Culture Collection (NRRL), Peoria, IL and have been assigned the listed accession numbers:

| E. Coli Strain | Plasmid | Accession Numbers |
|---|---|---|
| (All K12) | | |
| (1) MC1000 | pRV1 | B-15576 |
| (2) MC1000 | pRV51 | B-15577 |
| (3) MC1000 | pRV134 | B-15578 |
| (4) NF1829 | pRVE-451 | B-15579 |
| (5) NF1829 | pRVE-414-51 | B-15580 |
| (6) NF1829 | pCJRV134-P | B-15581 |
| (7) NF1829 | pJSRV134-HpX | B-15582 |
| (8) SK107F'iq | ptRV—BH | B-15843 |
| (9) NF1829 | pHKRV—106St | B-15845 |
| (10) NF1829 | ptRV—106S | B-15842 |
| (11) SK107F' | ptRV—12T | B-15844 |
| (12) MC1000 | pRV112 | B-15841 |
| (13) MC1000 | pRV106 | B-15840 |

The present invention is not to be limited in scope by the microorganism deposited, since the deposited embodiment is intended as a single illustration of one aspect of the invention. Indeed, various modifications of the invention in addition to those shown and described herein will become apparent to those skilled in the art from the foregoing description and accompanying drawings. Such modifications are intended to fall within the scope of the appended claims.

We claim:

1. A purified DNA sequence coding for the M portion of the Rift Valley fever virus genome as depicted in FIGS. 2a, 2b and 2c or any portion thereof coding for an immunoreactive and antigenic determinant of a Rift Valley fever virus.

2. A recombinant DNA vector, comprising the DNA sequence of claim 1.

3. The recombinant vector according to claim 2, wherein the vector is pRV1.

4. The recombinant vector according to claim 2, wherein the vector is pRV51.

5. The recombinant vector according to claim 2 wherein the vector is pRV134.

6. The recombinant vector according to claim 2, wherein the vector is pRV106.

7. The recombinant vector according to claim 2, wherein the vector is pRV112.

8. The recombinant DNA vector according to claim 2, wherein the DNA sequence codes for a Rift Valley Fever Virus glycoprotein G2, or any protion thereof.

9. The recombinant DNA vector according to claim 2, wherein the DNA sequence codes for a Rift Valley Fever Virus glycoprotein G1, or any portion thereof.

10. The recombinant vector of claim 2, wherein said DNA sequence is under the control of expression control elements.

11. The recombinant vector according to claim 10, wherein the vector is ptRV-106S, or a mutant, recombinant, or genetically engineered derivative thereof.

12. The recombinant vector according to claim 10, wherein the vector is ptRV-BH, or a mutant, recombinant, or genetically engineered derivative thereof.

13. The recombinant vector according to claim 10, wherein the vector is ptRV-C12T, or a mutant, recombinant, or genetically engineered derivative thereof.

14. The recombinant DNA vector of claim 2, inserted on the pBR322 replicon.

15. The recombinant vector of claim 2, wherein said DNA sequence is inserted in the correct reading frame to a second DNA sequence coding for a protein.

16. The recombinant vector of claim 10, wherein said DNA sequence is inserted in the correct reading frame to a second DNA sequence coding for a protein.

17. The recombinant vector of claim 16, wherein the vector is pRVE451, or a mutant, recombinant, or genetically engineered derivative thereof.

18. The recombinant vector of claim 16, wherein the vector is pRVE414-51, or a mutant, recombinant, or genetically engineered derivative thereof.

19. The recombinant vector of claim 16, wherein the vector is pCJRV-134-P, or a mutant, recombinant, or genetically engineered derivative thereof.

20. The recombinant vector of claim 16, wherein the vector is pJSRV-134HpX, or a mutant, recombinant, or genetically engineered derivative thereof.

21. The recombinant vector of claim 16, wherein the vector is pHKRV-106St, or a mutant, recombinant, or genetically engineered derivative thereof.

22. A unicellular organism containing the recombinant vector of claim 2.

23. A unicellular organism containing the recombinant vector of claim 8.

24. A unicellular organism containing the recombinant vector of claim 9.

25. A unicellular organism containing the recombinant vector of claim 10.

26. A unicellular organism containing the recombinant vector of claim 14.

27. A unicellular organism containing the recombinant vector of claim 15.

28. A unicellular organism containing the recombinant vector of claim 16.

29. An *Eschericha coli* bacterium containing the recombinant vector of claim 2.

30. An *Escherichia coli* bacterium containing the recombinant vector of claim 8.

31. An *Escherichia coli* bacterium containing the recombinant vector of claim 9.

32. An *Escherichia coli* bacterium containing the recombinant vector of claim 10.

33. An *Escherichia coli* bacterium containing the recombinant vector of claim 14.

34. An *Escherichia coli* bacterium containing the recombinant vector of claim 15.

35. An *Escherichia coli* bacterium containing the recombinant vector of claim 16.

36. The *Escherichia coli* bacterium of claim 29 deposited with the NRRL and assigned Accession No. B-15576, or a mutant, recombinant, or genetically engineered derivative thereof.

37. The *Escherichia coli* bacterium of claim 29 deposited with the NRRL and assigned Accession No. B-15577, or a mutant, recombinant, or genetically engineered derivative thereof.

38. The *Escherichia coli* bacterium of claim 29 deposited with the NRRL and assigned Accession No. B-15578, or a mutant, recombinant, or genetically engineered derivative thereof.

39. The *Escherichia coli* bacterium of claim 29 deposited with the NRRL and assigned Accession No. B-15840, or a mutant, recombinant, or genetically engineered derivative thereof.

40. The *Escherichia coli* bacterium of claim 29 deposited with the NRRL and assigned Accession No. B-15841, or a mutant, recombinant, or genetically engineered derivative thereof.

41. The *Escherichia coli* bacterium of claim 30 deposited with the NRRL and assigned Accession No. B-15579, or a mutant, recombinant, or genetically engineered derivative thereof.

42. The *Escherichia coli* bacterium of claim 30 deposited with the NRRL and assigned Accession No. B-15580, or a mutant, recombinant, or genetically engineered derivative thereof.

43. The *Escherichia coli* bacterium of claim 30 deposited with the NRRL and assigned Accession No. B-15843, or a mutant, recombinant, or genetically engineered derivative thereof.

44. The *Escherichia coli* bacterium of claim 30 deposited with the NRRL and assigned Accession No. B-15844, or a mutant, recombinant, or genetically engineered derivative thereof.

45. The *Escherichia coli* bacterium of claim 31 deposited with the NRRL and assigned Accession No. B-15581, or a mutant, recombinant, or genetically engineered derivative thereof.

46. The *Escherichia coli* bacterium of claim 31 deposited with the NRRL and assigned Accession No. B-15582, or a mutant, recombinant, or genetically engineered derivative thereof.

47. The *Escherichia coli* bacterium of claim 31 deposited with the NRRL and assigned Accession No. B-15845, or a mutant, recombinant, or genetically engineered derivative thereof.

48. The *Escherichia coli* bacterium of claim 34 deposited with the NRRL and assigned Accession No. B-15842, or a mutant, recombinant, or genetically engineered derivative thereof.

49. A vaccine formulation comprising a lysate of the unicellular organism of claim 25.

50. The vaccine formulation according to claim 49 further comprising a compatible pharmaceutical carrier therefor.

51. A vaccine formulation comprising a lysate of the *Escherichia coli* of claim 32.

52. The vaccine formulation according to claim 51 further comprising a compatible pharmaceutical carrier therefor.

53. A vaccine formulation comprising a lysate of the *Escherichia coli* of claim 41.

54. The vaccine formulation according to claim 53 further comprising a compatible pharmaceutical carrier therefor.

55. A vaccine formulation comprising a lysate of the *Escherichia coli* of claim 42.

56. The vaccine formulation according to claim 55 further comprising a compatible pharmaceutical carrier therefor.

57. A vaccine formulation comprising a lysate of the *Escherichia coli* of claim 43.

58. The vaccine formulation according to claim 57 further comprising a compatible pharamceutical carrier therefor.

59. A vaccine formulation comprising a lysate of the *Escherichia coli* of claim 44.

60. The vaccine formulation according to claim 59 further comprising a compatible pharmaceutical carrier therefor.

61. A vaccine formulation comprising a lysate of the *Escherichia coli* of claim 45.

62. The vaccine formulation according to claim 61 further comprising a compatible pharmaceutical carrier therefor.

63. A vaccine formulation comprising a lysate of the *Escherichia coli* of claim 46.

64. The vaccine formulation according to claim 63 further comprising a compatible pharmaceutical carrier therefor.

65. A vaccine formulation comprising a lysate of the *Escherichia coli* of claim 47.

66. The vaccine formulation according to claim 65 further comprising a compatible pharmaceutical carrier therefor.

67. A vaccine formulation comprising a lysate of the *Escherichia coli* of claim 48.

68. The vaccine formulation according to claim 67 further comprising a compatible pharmaceutical carrier therefor.

69. A vaccine formulation comprising a cell extract of the unicellular organism of claim 25.

70. The vaccine formulation according to claim 69 further comprising a compatible pharmaceutical carrier therefor.

71. A vaccine formulation comprising a cell extract of the *Escherichia coli* of claim 32.

72. The vaccine formulation according to claim 71 further comprising a compatible pharmaceutical carrier therefor.

73. A vaccine formulation comprising a cell extract of the *Escherichia coli* of claim 41.

74. The vaccine formulation according to claim 73 further comprising a compatible pharmaceutical carrier therefor.

75. A vaccine formulation comprising a cell extract of the *Escherichia coli* of claim 42.

76. The vaccine formulation according to claim 75 further comprising a compatible pharmaceutical carrier therefor.

77. A vaccine formulation comprising a cell extract of the *Escherichia coli* of claim 43.

78. The vaccine formulation according to claim 77 further comprising a compatible pharmaceutical carrier therefor.

79. A vaccine formulation comprising a cell extract of the *Escherichia coli* of claim 44.

80. The vaccine formulation according to claim 79 further comprising a compatible pharmaceutical carrier therefor.

81. A vaccine formulation comprising a cell extract of the *Escherichia coli* of claim 45.

82. The vaccine formulation according to claim 81 further comprising a compatible pharmaceutical carrier therefor.

83. A vaccine formulation comprising a cell extract of the *Escherichia coli* of claim 46.

84. The vaccine formulation according to claim 83 further comprising a compatible pharmaceutical carrier therefor.

85. A vaccine formulation comprising a cell extract of the *Escherichia coli* of claim 47.

86. The vaccine formulation according to claim 85 further comprising a compatible pharmaceutical carrier therefor.

87. A vaccine formulation comprising a cell extract of the *Escherichia coli* of claim 48.

88. The vaccine formulation according to claim 87 further comprising a compatible pharmaceutical carrier therefor.

* * * * *